(12) United States Patent
Dong et al.

(10) Patent No.: US 10,457,631 B2
(45) Date of Patent: Oct. 29, 2019

(54) BIODEGRADABLE AMINO-ESTER NANOMATERIALS FOR NUCLEIC ACID DELIVERY

(71) Applicant: OHIO STATE INNOVATION FOUNDATION, Columbus, OH (US)

(72) Inventors: Yizhou Dong, Dublin, OH (US); Xinfu Zhang, Columbus, OH (US); Xiao Luo, Derwood, MD (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 16/091,062

(22) PCT Filed: Apr. 6, 2017

(86) PCT No.: PCT/US2017/026320
§ 371 (c)(1),
(2) Date: Oct. 3, 2018

(87) PCT Pub. No.: WO2017/176974
PCT Pub. Date: Oct. 12, 2017

(65) Prior Publication Data
US 2019/0119198 A1   Apr. 25, 2019

Related U.S. Application Data

(60) Provisional application No. 62/398,732, filed on Sep. 23, 2016, provisional application No. 62/319,089, filed on Apr. 6, 2016.

(51) Int. Cl.
   C07C 229/16   (2006.01)
   A61K 47/18    (2017.01)
   A61K 48/00    (2006.01)

(52) U.S. Cl.
   CPC ............ *C07C 229/16* (2013.01); *A61K 47/18* (2013.01); *A61K 48/0008* (2013.01)

(58) Field of Classification Search
   None
   See application file for complete search history.

(56) References Cited

U.S. PATENT DOCUMENTS

| | | |
|---|---|---|
| 2012/0136073 A1 | 5/2012 | Yang et al. |
| 2014/0161830 A1 | 6/2014 | Anderson et al. |
| 2015/0306039 A1 | 10/2015 | Akinc et al. |
| 2015/0376115 A1 | 12/2015 | Ansell et al. |

OTHER PUBLICATIONS

International Search Report and Written Opinion of the U.S. International Searching Authority. Application No. PCT/US2017/026320, dated Jun. 22, 2017. 17 pages.
PUBCHEM. NSC100266. Mar. 26, 2005, pp. 1-11 [online]. Retrieved Dec. 23, 2013 from <URL: https://pubchem.ncbi.nlm.nih.gov/compound/264873#section=Top.
Akinc A, Goldberg M, Qin J, Dorkin JR, Gamba-Vitalo C, Maier M, et al. Development of lipidoid-siRNA formulations for systemic delivery to the liver. Mol Ther. 2009;17(5):872-9.
Akinc A, Zumbuehl A, Goldberg M, Leshchiner ES, Busini V, Hossain N, et al. A combinatorial library of lipid-like materials for delivery of RNAi therapeutics. Nat Biotechnol. 2008;26(5):561-9.
Alabi CA, Love KT, Sahay G, Stutzman T, Young WT, Langer R, et al. FRET-labeled siRNA probes for tracking assembly and disassembly of siRNA nanocomplexes. ACS Nano. 2012;6(7):6133-41.
Alabi CA, Love KT, Sahay G, Yin H, Luly KM, Langer R, et al. Multiparametric approach for the evaluation of lipid nanoparticles for siRNA delivery. Proc Natl Acad Sci U S A. 2013;110(32):12881-6.
Altschul et al. Gapped BLAST and PSI-BLAST: a new generation of protein database search programs. Nuc. Acids Res. 1977, 25:3389-3402.
Altschul et al. Basic local alignment search tool. J. Mol. Biol. 1990, 215:403-410.
Barros SA, Gollob JA. Safety profile of RNAi nanomedicines. Adv Drug Deliv Rev. 2012;64(15):1730-7.
Barzel A, Paulk NK, Shi Y, Huang Y, Chu K, Zhang F, et al. Promoterless gene targeting without nucleases ameliorates haemophilia B in mice. Nature. 2015;517(7534):360-4.
Beaucage and Carruthers, Deoxynucleoside phosphoramidites—a new class of key intermediates for deoxypolynucleotide synthesis. Tetrahedron Lett., 22:1859-1862, 1981.
Boshart et al, A very strong enhancer is located upstream of an immediate early gene of human cytomegalovirus. Cell, 41:521-530, 1985.
Burnett, J. C., J. J. Rossi, and K. Tiemann, Current progress of siRNA/shRNA therapeutics in clinical trials. Biotechnol J. 6(9): p. 1130-46.
Castanotto, D. and J. J. Rossi, The promises and pitfalls of RNA-interference-based therapeutics. Nature, 2009. 457(7228): p. 426-33.
Chang, C. Sun, L. Gao, D. Zhu, X. Xu, X. Zhu, J. Xiong, J. Xi, Genome editing with RNA-guided Cas9 nuclease in zebrafish embryos. Cell Res. 2013, 23, 465.
Chen D, Love KT, Chen Y, Eltoukhy AA, Kastrup C, Sahay G, et al. Rapid Discovery of Potent siRNA-Containing Lipid Nanoparticles Enabled by Controlled Microfluidic Formulation. J Am Chem Soc. 2012;134(16):6948-51.
Chen S, Sanjana Ne, Zheng K, Shalem 0, Lee K, Shi X, et al. Genome-wide CRISPR screen in a mouse model of tumor growth and metastasis. Cell. 2015;160(6):1246-60.
Chen, Y. and L. Huang, Tumor-targeted delivery of siRNA by non-viral vector: safe and effective cancer therapy. Expert Opin Drug Deliv, 2008. 5(12): p. 1301-11.
Coelho, T., Familial amyloid polyneuropathy: new developments in genetics and treatment. Curr Opin Neurol, 1996. 9(5): p. 355-9.
Cong L, Ran FA, Cox D, Lin S, Barretto R, Habib N, et al. Multiplex genome engineering using CRISPR/Cas systems. Science. 2013;339(6121):819-23.

(Continued)

*Primary Examiner* — Alicia L Otton
(74) *Attorney, Agent, or Firm* — Meunier Carlin & Curfman LLC

(57) ABSTRACT

The present disclosure relates to a series of biodegradable amino-ester lipid-like nanoparticles. In some embodiments, the biodegradable amino-ester lipid-like nanoparticles are used in methods for the delivery of nucleic acids.

20 Claims, 10 Drawing Sheets

(56) References Cited

OTHER PUBLICATIONS

Coppola A, Di Capua M, Di Minne MN, Di Palo M, Marrone E, Ierano P, et al. Treatment of hemophilia: a review of current advances and ongoing issues. Journal of blood medicine. 2010;1:183-95.
Cui WG, Li XH, Zhou SB, Weng J. Investigation on process parameters of electrospinning system through orthogonal experimental design. J Appl Polym Sci. 2007;103(5):3105-12.
Dahlman JE, Barnes C, Khan OF, Thiriot A, Jhunjunwala S, Shaw TE, et al. In vivo endothelial siRNA delivery using polymeric nanoparticles with low molecular weight. Nat Nanotechnol. 2014;9(8):648-55.
Damian M, Porteus MH. A crisper look at genome editing: RNA-guided genome modification. Mol Ther. 2013;21(4):720-2.
Davis, M. E., The first targeted delivery of siRNA in humans via a self-assembling, cyclodextrin polymer-based nanoparticle: from concept to clinic. Mol Pharm, 2009. 6(3): p. 659-68.
Dong Y, Eltoukhy AA, Alabi CA, Khan OF, Veiseh 0, Dorkin JR, et al.Lipid-like nanomaterials for simultaneous gene expression and silencing in vivo. Advanced healthcare materials. 2014;3(9):1392-7.
Dong Y, Love KT, Dorkin JR, Sirirungruang S, Zheng Y, Chen D, et al. Lipopeptide nanoparticles for potent and selective siRNA delivery in rodents and nonhuman primates. Proc Natl Acad Sci U S A. 2014;111(11):3955-60.
Dong, J. R. Dorkin, W. Wang, P. H. Chang, M. J. Webber, B. C. Tang, J. Yang, I. Abutbul-Ionita, D. Danino, F. DeRosa, M. Heartlein, R. Langer, D. G. Anderson, Poly(glycoamidoamine) Brushes Formulated Nanomaterials for Systemic siRNA and mRNA Delivery in Vivo. Nano Lett. 2016, 16, 842-8.
Fenske, D. B. and P. R. Cullis, Liposomal nanomedicines. Expert Opin Drug Deliv, 2008. 5(1): p. 25-44.
Fenton, K. J. Kauffman, R. L. McClellan, E. A. Appel, J. R. Dorkin, M. W. Tibbitt, M. W. Heartlein, F. DeRosa, R. Langer, D. G. Anderson, Bioinspired alkenyl amino alcohol ionizable lipid materials for highly potent in vivo mRNA delivery. Adv. Mater. 2016, 28, 2939-2943.
Fire, A., et al., Potent and specific genetic interference by double-stranded RNA in Caenorhabditis elegans. Nature, 1998. 391(6669): p. 806-11.
Frank-Kamenetsky, M., et al., Therapeutic RNAi targeting PCSK9 acutely lowers plasma cholesterol in rodents and LDL cholesterol in nonhuman primates. Proc Natl Acad Sci USA, 2008. 105(33): p. 11915-20.
Friedland, R. Baral, P. Singhal, K. Loveluck, S. Shen, M. Sanchez, E. Marco, G. M. Gotta, M. L. Maeder, E. M. Kennedy, A. V. R. Kornepati, A. Sousa, M. A. Collins, H. Jayaram, B. R. Cullen, D. Bumcrot, Genome Biol. 2015, 16, 257.
Fu, J. A. Foden, C. Khayter, M. L. Maeder, D. Reyon, J. K. Joung, J. D. Sander, Nat. Biotechnol. 2013, 31, 822.
Gao, Y. K. Kim, C. Zhang, V. Borshch, S. Zhou, H. S. Park, A. Jákli, O. D. Lavrentovich, M. G. Tamba, A. Kohlmeier, G. H. Mehl, W. Weissflog, D. Studer, B. Zuber, H. Gnägi, F. Lin, Direct observation of liquid crystals using cryo-TEM: specimen preparation and low-dose imaging. Microsc. Res. Tech. 2014, 77, 754.
Henikoff and Henikoff (1989) Amino acid substitution matrices from protein blocks. Proc. Natl. Acad. Sci. USA 89:10915.
Hsu PD, Scott DA, Weinstein JA, Ran FA, Konermann S, Agarwala V, et al. DNA targeting specificity of RNA-guided Cas9 nucleases. Nat Biotechnol. 2013;31(9):827-32.
Jinek M, Chylinski K, Fonfara I, Hauer M, Doudna JA, Charpentier E. A programmable dual-RNA-guided DNA endonuclease in adaptive bacterial immunity. Science. 2012;337(6096): 816-21.
Juliano, R., et al., Biological barriers to therapy with antisense and siRNA oligonucleotides. Mol Pharm, 2009. 6(3): p. 686-95.
Kanasty, J. R. Dorkin, A. Vegas, D. Anderson, Delivery materials for siRNA therapeutics. Nat. Mater. 2013, 12, 967.
Kariko, H. Muramatsu, J. M. Keller, D. Weissman, Increased erythropoiesis in mice injected with submicrogram quantities of pseudouridine-containing mRNA encoding erythropoietin. Mol. Ther. 2012, 20, 948.
Karlin and Altschul (1993) Applications and statistics for multiple high-scoring segments in molecular sequences. Proc. Natl. Acad. Sci. USA 90:5873-5787.
Kauffman, J. R. Dorkin, J. H. Yang, M. W. Heartlein, F. DeRosa, F. F. Mir, O. S. Fenton, D. G. Anderson, Optimization of Lipid Nanoparticle Formulations for mRNA Delivery in Vivo with Fractional Factorial and Definitive Screening Designs. Nano Lett. 2015, 15,7300.
Kim H, Kim JS. A guide to genome engineering with programmable nucleases. Nat Rev Genet. 2014;15(5):321-34.
Leachman, S. A., et al., Therapeutic siRNAs for dominant genetic skin disorders including pachyonychia congenita. J Dermatol Sci, 2008. 51(3): p. 151-7.
Li, X. Luo, B. Deng, J. Wang, D. W. McComb, Y. Shi, K. M. L. Gaensler, X. Tan, A. L. Dunn, B. A. Kerlin, Y. Dong, An Orthogonal Array Optimization of Lipid-like Nanoparticles for mRNA Delivery in Vivo. Nano Lett. 2015, 15, 8099.
Love Kevin T, Mahon Kerry P, Levins Christopher G, Whitehead Kathryn A, Querbes W, Dorkin JR, et al. Lipid-like materials for low-dose, in vivo gene silencing. Proc Natl Acad Sci U S A. 2010;107(5): 1864-9.
Maier, M. Jayaraman, S. Matsuda, J. Liu, S.t Barros, W. Querbes, Y. K Tam, S. M. Ansell, V. Kumar. J. Qin. X. Zhang, Q. Wang, S. Panesar, R. Hutabarat, M. Carioto, J. Hettinger, P. Kandasamy, D. Butler, K. G. Rajeev, B. Pang, K. Charisse, K. Fitzgerald, B. L Mui, X. Du, P. Cullis, T. D. Madden, M. J. Hope, M. Manoharan, A. Akinc, Biodegradable Lipids Enabling Rapidly Eliminated Lipid Nanoparticles for Systemic Delivery of RNAi Therapeutics. Mol. Ther. 2013, 21, 1570.
Mali P, Esvelt KM, Church GM. Cas9 as a versatile tool for engineering biology. Nat Methods. 2013;10(10):957-63.
Mali P, Yang L, Esvelt KM, Aach J, Guell M, DiCarlo JE, et al. RNA-guided human genome engineering via Cas9. Science. 2013;339(6121 ):823-6.
Marks JR, Placone J, Hristova K, Wimley WC. Spontaneous membrane-translocating peptides by orthogonal high-throughput screening. J Am Chem Soc. 2011;133(23):8995-9004.
Martin EJ, Blaney JM, Siani MA, Spellmeyer DC, Wong AK, Moos WH. Measuring diversity: experimental design of combinatorial libraries for drug discovery. J Med Chem. 1995;38(9):1431-6.
Matteucci, et al., Synthesis of deoxyoligonucleotides on a polymer support. J. Am. Chem. Soc., 103:3185, 1981.
McClellan, J. and M. C. King, Genetic heterogeneity in human disease. Cell. 141(2): p. 210-7.
Mcivor RS. Therapeutic delivery of mRNA: the medium is the message. Mol Ther. 2011;19(5):822-3.
Takebe, M Seiki, J Fujisawa, P Hoy, K Yokota, K Arai, M Yoshida, N Arai, SR alpha promoter: an efficient and versatile mammalian cDNA expression system composed of the simian virus 40 early promoter and the R-U5 segment of human T-cell leukemia virus type 1 long terminal repeat. Mol. Cell. Biol., vol. 8(1), p. 466-472, 1988.
Monahan PE, White GC, 2nd. Hemophilia gene therapy: update. Current opinion in hematology. 2002;9(5):430-6.
O'Hare, et al., Transformation of mouse fibroblasts to methotrexate resistance by a recombinant plasmid expressing a prokaryotic dihydrofolate reductase. Proc. Natl. Acad. Sci. USA., vol. 78(3), p. 1527-31, 1981.
O'Connell MR, Oakes BL, Sternberg SH, East-Seletsky A, Kaplan M, Doudna JA. Programmable RNA recognition and cleavage by CRISPR/Cas9. Nature. 2014;516(7530):263-6.
Oda, H.Yamashita, K. Kosahara, S. Kuroki, F. Nakayama, Esterified and total 7 alpha-hydroxycholesterol in human serum as an indicator for hepatic bile acid synthesis. J. Lipid Res. 1990, 31, 2209.
Pascolo S. Vaccination with messenger RNA (mRNA). Handb Exp Pharmacol. 2008(183):221-35.
Phua KK, Leong KW, Nair SK. Transfection efficiency and transgene expression kinetics of mRNA delivered in naked and nanoparticle format. J Control Release. 2013;166(3):227-33.

(56) References Cited

OTHER PUBLICATIONS

Platt, S. Chen, Y. Zhou, M. J. Yim, L. Swiech, H. R. Kempton, J. E. Dahlman, O. Parnas, T. M. Eisenhaure, M. Jovanovic, D. B. Graham, S. Jhunjhunwala, M. Heidenreich, R. J. Xavier, R. Langer, D. G. Anderson, N. Hacohen, A. Regev, G. Feng, P. A. Sharp, F. Zhang, CRISPR-Cas9 Knockin Mice for Genome Editing and Cancer Modeling. Cell, 2014, 159, 440.

Rajabi, M. Lanfranchi, F. Campo, L. Panza, Synthesis of a Series of Hydroxycarboxylic Acids as Standards for Oxidation of Nonanoic Acid. Synth. Commun. 2014, 44, 1149.

Ran FA, Cong L, Yan WX, Scott DA, Gootenberg JS, Kriz AJ, et al. In vivo genome editing using *Staphylococcus aureus* Cas9. Nature. 2015;520(7546): 186-91.

Ran FA, Hsu PD, Lin CY, Gootenberg JS, Konermann S, Trevino AE, et al. Double nicking by RNA-guided CRISPR Cas9 for enhanced genome editing specificity. Cell. 2013;154(6):1380-9.

Ryan D, Papamichail D. Rational Design of Orthogonal Libraries of Protein Coding Genes. Acs Synth Biol. 2013;2(5):237-44.

Sabatino DE, Nichols TC, Merricks E, Bellinger DA, Herzog RW, Monahan PE. Animal models of hemophilia. Progress in molecular biology and translational science. 2012;105:151-209.

Sahin U, Kariko K, Tureci 0. mRNA-based therapeutics—developing a new class of drugs. Nat Rev Drug Discov. 2014;13(10):759-80.

Sander JD, Joung JK. CRISPR-Cas systems for editing, regulating and targeting genomes. Nat Biotechnol. 2014;32(4):347-55.

Semple SC, Akinc A, Chen J, Sandhu AP, Mui BL, Cho CK, et al. Rational design of cationic lipids for siRNA delivery. Nat Biotechnol. 2010;28(2):172-6.

Shalem O, Sanjana NE, Hartenian E, Shi X, Scott DA, Mikkelsen TS, et al. Genome-scale CRISPR-Cas9 knockout screening in human cells. Science. 2014;343(6166):84-7.

Sternberg SH, Redding S, Jinek M, Greene EC, Doudna JA. DNA interrogation by the CRISPR RNA-guided endonuclease Cas9. Nature. 2014;507(7490):62-7.

Su X, Fricke J, Kavanagh DG, Irvine DJ. In vitro and in vivo mRNA delivery using lipid-enveloped pH-responsive polymernanoparticles. Mol Pharm. 2011;8(3):774-87.

Sun, W. Ji, J. M. Hall, Q. Hu, C. Wang, C. L. Beisel, Z. Gu, Angew. Chem. Int. Ed. 2015, 54, 12029.

Suwanmanee T, Hu G, Gui T, Bartholomae CC, Kutschera I, von Kalle C, et al. Integration-deficient lentiviral vectors expressing codon-optimized R338L human FIX restore normal hemostasis in Hemophilia B mice. Mol Ther. 2014;22(3):567-74.

Woodcock, A. J. V. Marwitz, P. Bruno, B. P. Branchaud, Synthesis of Nitrolipids. All Four Possible Diastereomers of Nitrooleic Acids: (E)- and (Z)-, 9- and 10-Nitro-octadec-9-enoic Acids. Org. Lett. 2006, 8, 3931.

Tan, S. J., et al., Engineering Nanocarriers for siRNA Delivery. Small. 7(7): p. 841-56.

Tavernier G, Andries 0, Demeester J, Sanders NN, De Smedt SC, Rejman J. mRNA as gene therapeutic: how to control protein expression. J Control Release. 2011;150(3):238-47.

Thiel, K. W. and P. H. Giangrande, Therapeutic Applications of DNA and RNA aptamers. Oligonucleotides, 2009. 19(3): p. 209-22.

Wang, L. et al. A factor IX-deficient mouse model for hemophilia B gene therapy. Proc. Natl. Acad. Sci. U. S. A.1997, 94, 11563-11566.

Weinstein, S, and D. Peer, RNAi nanomedicines: challenges and opportunities within the immune system. Nanotechnology. 2010, 21(23): p. 232001.

Whitehead, J. R. Dorkin, A. J. Vegas, P. H. Chang, O. Veiseh, J. Matthews, O. S. Fenton, Y. Zhang, K. T. Olejnik, V. Yesilyurt, D. Chen, S. Barros, B. Klebanov, T. Novobrantseva, R. Langer, D. G. Anderson, Nat. Commun. 2014, 5, 4277.

Whitehead, K. A., R. Langer, and D. G. Anderson, Knocking down barriers: advances in siRNA delivery. Nat. Rev. Drug Discovery, 2009. 8(2): p. 129-138.

Yin H, Xue W, Chen S, Bogorad RL, Benedetti E, Grompe M, et al. Genome editing with Cas9 in adult mice corrects a disease mutation and phenotype. Nat Biotechnol. 2014;32(6):551-3.

Yin, C. Song, J. R. Dorkin, L. J. Zhu, Y. Li, Q. Wu, A. Park, J. Yang, S. Suresh, A. Bizhanova, A. Gupta, M. F. Bolukbasi, S. Walsh, R. L. Bogorad, G. Gao, Z. Weng, Y. Dong, V. Koteliansky, S. A. Wolfe, R. Langer, W. Xue, D. G. Anderson, Therapeutic genome editing by combined viral and non-viral delivery of CRISPR system components in vivo. Nat. Biotechnol. 2016, 33, 328-33.

Zhan JY, Zheng KY, Zhu KY, Bi CW, Zhang WL, Du CY, et al. Chemical and biological assessment of Angelicae Sinensis Radix after processing with wine: an orthogonal array design to reveal the optimized conditions. J Agric Food Chem. 2011;59(11):6091-8.

Zincarelli C, Soltys S, Rengo G, Rabinowitz JE. Analysis of AAV serotypes 1-9 mediated gene expression and tropism in mice after systemic injection. Mol Ther. 2008;16(6):1073-80.

Zuris JA, Thompson DB, Shu Y, Guilinger JP, Bessen JL, Hu JH, et al. Cationic lipid-mediated delivery of proteins enables efficient protein-based genome editing in vitro and in vivo. Nat Biotechnol. 2015;33(1):73-80.

International Preliminary Report on Patentability issued for Application No. PCT/US2017/026320, dated Oct. 18, 2018, 15 pages.

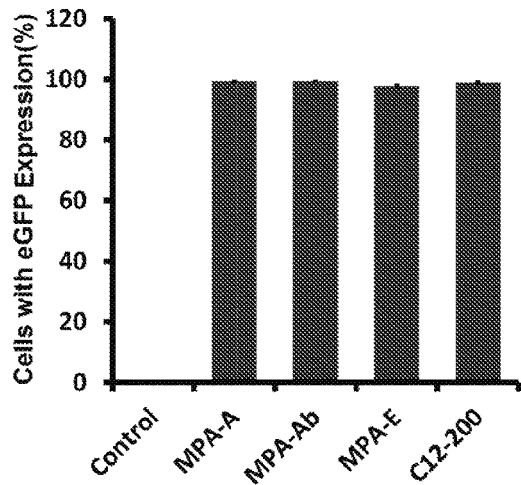
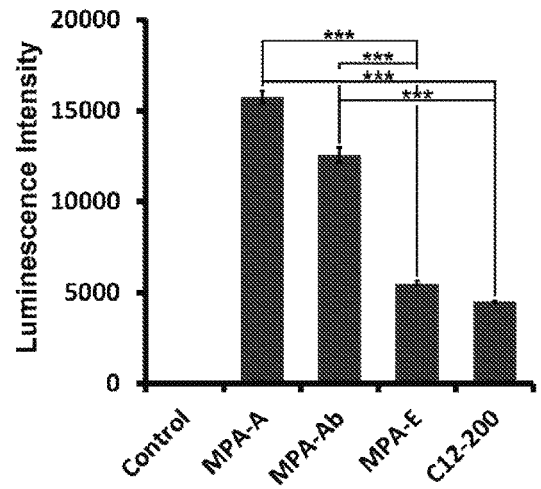
FIG. 7A                FIG. 7B
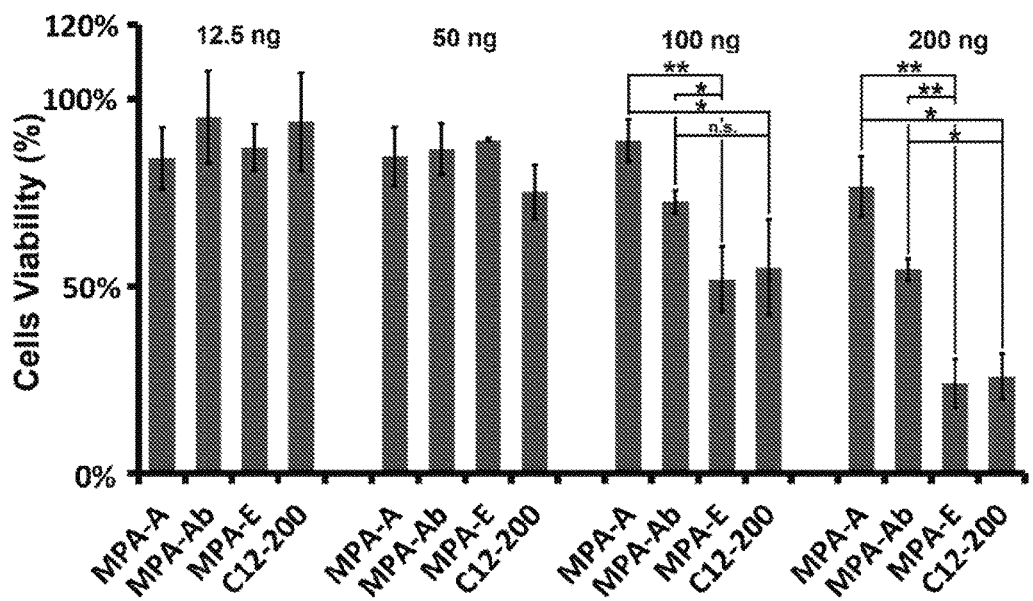
FIG. 8

BIODEGRADABLE AMINO-ESTER NANOMATERIALS FOR NUCLEIC ACID DELIVERY

CROSS-REFERENCE TO RELATED APPLICATIONS

This application is a national stage application filed under 35 U.S.C. § 371 of PCT/US2017/026320 filed Apr. 6, 2017, which claims the benefit of U.S. Provisional Patent Application Ser. No. 62/319,089 filed Apr. 6, 2016, and U.S. Provisional Patent Application Ser. No. 62/398,732 filed Sep. 23, 2016, each of which are expressly incorporated herein by reference.

STATEMENT REGARDING FEDERALLY SPONSORED RESEARCH

This invention was made with Government Support under Grant No. 1R01HL136652 awarded by the National Heart, Lung, and Blood Institute. The Government has certain rights to the invention.

FIELD

The present disclosure relates to compounds, compositions, lipid-like nanoparticles, and methods for delivery of therapeutic, diagnostic, or prophylactic agents (for example, a polynucleotide).

BACKGROUND

CRISPR/Cas9 mediated genome editing has been widely used as a powerful tool for biological and therapeutic applications. Adeno-associated virus (AAV) derived vectors and DNA nanoclews were reported to deliver plasmid-encoding CRISPR/Cas in a wide variety of cells and animal models. Yet, potential off-target effects are significant safety issues if Cas9 is present for long term. One alternative approach is to express Cas9 protein using Cas9 mRNA; however, efficient delivery of Cas9 mRNA is formidable due to its large size (up to 4.5 k nucleotides), high density of negative charges, and weak tolerance of enzymes in serum. Hence, new biomaterials are needed to overcome this obstacle and enable broad applications for delivering nucleic acids, for example, nucleic acids for use in the CRISPR/Cas9 gene editing system.

Messenger RNA (mRNA) based therapeutics have shown great promise for expressing functional antibodies and proteins. Clinical studies have explored mRNA for use as vaccines through local administration of naked mRNA or mRNA-transfected dendritic cells in order to induce antigen-specific immune responses. Recently, extensive efforts have been devoted to achieving the systemic delivery of mRNA using liposomes, polymeric nanoparticles, and mRNA-protein complexes. Although significant advances have been made, new mRNA carriers are needed in order to improve delivery efficiency and maximize therapeutic windows of mRNA therapeutics in different human conditions.

Lipid and lipid-like nanoparticles (LNPs and LLNs) represent one type of biomaterial for efficient delivery of RNAs including siRNA, miRNA, and mRNA. Recently, a few lipid-like nanoparticle-based delivery systems demonstrated efficient delivery of mRNAs for expression of functional proteins including factor IX, erythropoietin and Cas9. However, these previous lipid-like compounds are not considered to be biodegradable, which may lead to potential side effects. Therefore, what is needed are materials with biodegradable bonds that enable rapid elimination from plasma and tissues, and that substantially improve their tolerability in preclinical studies.

The compounds, compositions, and methods disclosed herein address these and other needs.

SUMMARY

The present disclosure provides new amino ester compounds and uses thereof. Also provided are compositions including a compound of the invention and an agent (e.g., an mRNA). The present disclosure also provides methods and kits using the compositions for delivering an agent to a subject.

In one aspect, the disclosure provides compounds of Formula I:

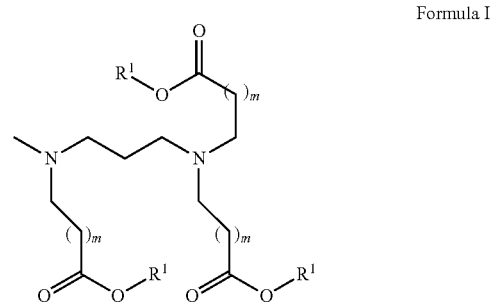

Formula I and salts thereof, wherein $R^1$ and m are as described herein.

In one aspect, the disclosure provides compounds of Formula II:

Formula II and salts thereof, wherein $R^1$ and m are as described herein.

In another aspect, the disclosure provides compounds of Formula III:

Formula III and salts thereof, wherein $R^1$ m are as described herein.

In a further aspect, the disclosure provides compounds of Formula IV:

Formula IV

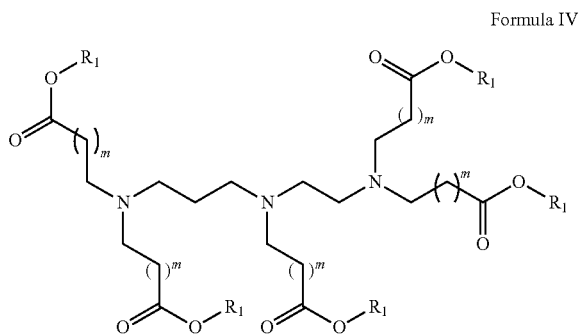

and salts thereof, wherein $R^1$ and m are as described herein.

In one aspect, the disclosure provides a nanoparticle comprising:
a compound of Formula I, II, III, or IV;
a non-cationic lipid;
a polyethylene glycol-lipid; and
a sterol.

In one embodiment, the disclosure provides a nanoparticle comprising:
a compound of Formula I, II, III, or IV;
1,2-dioleoyl-sn-glycero-3-phosphoethanolamine (DOPE);
1,2-dimyristoyl-sn-glycerol, methoxypolyethylene glycol (DMG-PEG$_{2000}$); and
a cholesterol.

In one aspect, provided herein is a method for the delivery of an agent (for example, a polynucleotide) into a cell comprising;
introducing into the cell a composition comprising;
i) a nanoparticle, comprising;
    a compound of Formula I, II, III, or IV;
    a non-cationic lipid;
    a polyethylene glycol-lipid;
    a sterol; and
ii) an agent.

In some embodiments, the agent is a therapeutic agent, diagnostic agent, or prophylactic agent. In some embodiments, the agent is a polynucleotide (for example, and mRNA).

In some embodiments, provided herein are methods for the delivery of polynucleotides. In some embodiments, provided herein are methods for the delivery of polynucleotides (for example, mRNA) to correct a mutation in a genome. For example, mRNAs can be delivered to correct mutations that cause hemophilia (due to mutations in the genes encoding Factor VIII (F8; hemophilia A) or Factor IX (F9; hemoglobin B).

BRIEF DESCRIPTION OF THE DRAWINGS

The accompanying figures, which are incorporated in and constitute a part of this specification, illustrate several aspects described below.

(FIG. 1A) Particle size. (FIG. 1B) Zeta potential. (FIG. 1C) Entrapment efficiency of Cas9 mRNA. (FIG. 1D) Delivery efficacy of Cas9 mRNA using amino-ester LLNs in vitro. (triplicate; , P<0.01; *, P<0.001; t test, double-tailed).

(FIG. 2A) Degradation rate in esterase solution: treated group with esterase (solid circle); PBS control without esterase (hollow circle). Over 53% of MPA-A was degraded after 24 h incubation, while 22% of MPA-Ab was degraded. No significant degradation was observed for MPA-E, a non-biodegradable control group. (triplicate; *, P<0.05; **, P<0.01; t test, double-tailed). (FIG. 2B) Cryo-TEM images of MPA-A and MPA-Ab LLNs. Scale bar: 100 nm.

(FIG. 4A) Phamarcokinetic Analysis of MPA-A and MPA-Ab. (FIG. 4B) Histology images of MPA-A and MPA-Ab FIG. 5. Dose-dependence of amino ester compounds. Delivery of Cas9 mRNA using MPA-A, MPA-Ab, C12-200 and MPA-E LLNs in vitro at dose of 100, 50, 25 and 12.5 ng. Control: PBS. (triplicate; *, P<0.05; , P<0.01; *, P<0.001; t test, double-tailed).

FIGS. 7A-7B. Delivery and expression of eGFP using amino ester nanoparticles. (FIG. 7A) Percentage of cells in population with eGFP expression. (FIG. 7B) Delivery of mRNA encoding eGFP in 293T cells. Control: PBS. (triplicate; ***, P<0.001; t test, double-tailed).

FIG. 8. Cell viability as measured in the MTT assay on 293T cell line at mRNA dose of 12.5, 50 100 and 200 ng. (triplicate; *, P<0.05; **, P<0.01; t test, double-tailed).

DETAILED DESCRIPTION

Figure 1A:
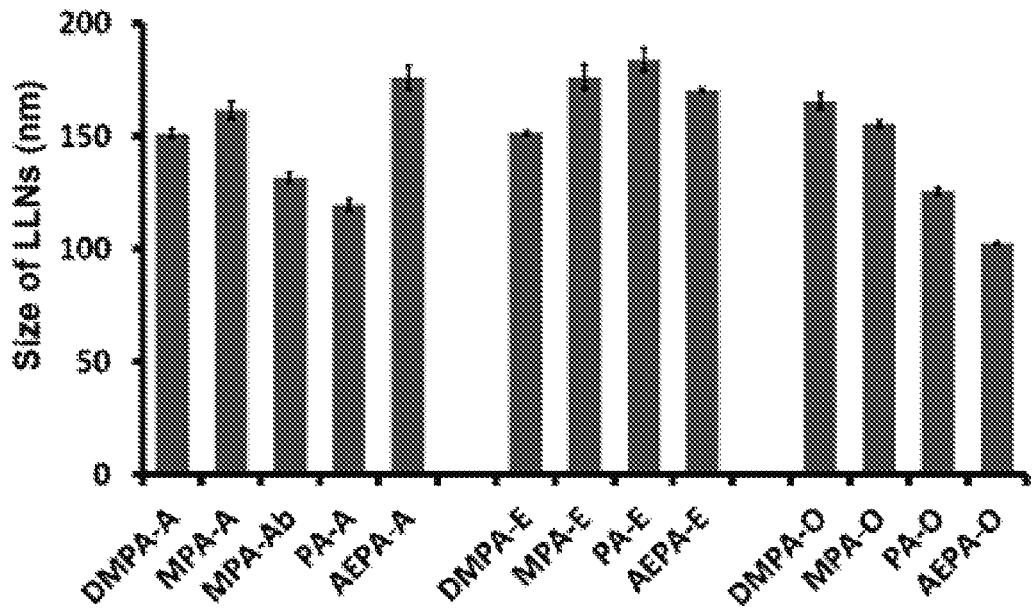
FIGS. 1A-1D. Characterizations of amino-ester lipid-like nanpparticles (LLNs).

The present disclosure provides new amino ester compounds and uses thereof. Also provided are compositions including a compound of the invention and an agent (e.g., an mRNA). The present disclosure also provides methods and kits using the compositions for delivering an agent to a subject.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this invention belongs. The following definitions are provided for the full understanding of terms used in this specification.

Terminology

As used herein, the article "a," "an," and "the" means "at least one," unless the context in which the article is used clearly indicates otherwise.

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22: 1859-1862 (1981), or by the triester method according to Matteucci, et al., *J. Am. Chem. Soc.*, 103: 3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "target" refers to a molecule that has an affinity for a given probe. Targets may be naturally-occurring or man-made molecules. Also, they can be employed in their unaltered state or as aggregates with other species.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein. The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, Gene Expression Technology: Methods in Enzymology 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol I promoters), one or more pol II promoters (e.g. 1, 2, 3, 4, 5, or more pol II promoters), one or more pol I promoters (e.g. 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It is appreciated by those skilled in the art that the design of the expression vector can depend on such factors as the choice of the host cell to be transformed, the level of expression desired, etc.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J Mol. Biol.* 215: 403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89: 10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

The term "nucleobase" refers to the part of a nucleotide that bears the Watson/Crick base-pairing functionality. The most common naturally-occurring nucleobases, adenine (A), guanine (G), uracil (U), cytosine (C), and thymine (T) bear the hydrogen-bonding functionality that binds one nucleic acid strand to another in a sequence specific manner.

As used throughout, by a "subject" (or a "host") is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as ($Z^1Z^2$)C=C($Z^3Z^4$) are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —NZ$^1$Z$^2$, where Z$^1$ and Z$^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O$^-$.

The term "ester" as used herein is represented by the formula —OC(O)Z$^1$ or —C(O)OZ$^1$, where Z$^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula Z$^1$OZ$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula Z$^1$C(O)Z$^2$, where Z$^1$ and Z$^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —NO$_2$.

The term "silyl" as used herein is represented by the formula —SiZ$^1$Z$^2$Z$^3$, where Z$^1$, Z$^2$, and Z$^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —S(O)$_2$Z$^1$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —S(O)$_2$NH—.

The term "phosphonyl" is used herein to refer to the phospho-oxo group represented by the formula —P(O)(OZ$^1$)$_2$, where Z$^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "thiol" as used herein is represented by the formula —SH.

The term "thio" as used herein is represented by the formula —S—.

"R$^1$," "R$^2$," "R$^3$," "R$^n$," etc., where n is some integer, as used herein can, independently, possess one or more of the groups listed above. For example, if R$^1$ is a straight chain alkyl group, one of the hydrogen atoms of the alkyl group can optionally be substituted with a hydroxyl group, an alkoxyl group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

In one aspect, disclosed herein is a compound of Formula I:

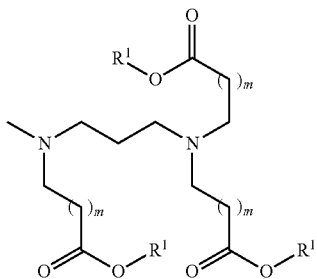

Formula I and salts thereof; wherein
each $R^1$ is independently substituted or unsubstituted alkyl; or substituted or unsubstituted alkenyl; and
each m is independently 3, 4, 5, 6, 7, 8, 9, or 10.

In one aspect, disclosed herein is a compound of Formula II:

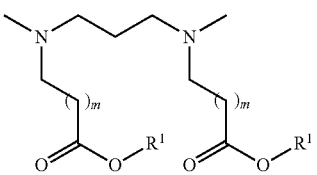

Formula II and salts thereof; wherein
each $R^1$ is independently substituted or unsubstituted alkyl; or substituted or unsubstituted alkenyl; and
each m is independently 3, 4, 5, 6, 7, 8, 9, or 10.

In one aspect, disclosed herein is a compound of Formula III:

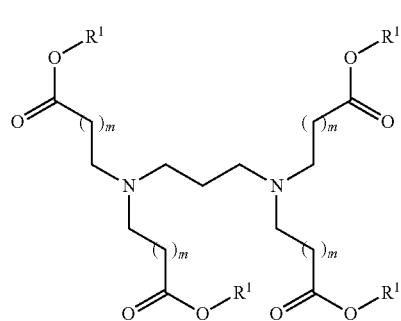

Formula III and salts thereof; wherein
each $R^1$ is independently substituted or unsubstituted alkyl; or substituted or unsubstituted alkenyl; and
each m is independently 3, 4, 5, 6, 7, 8, 9, or 10.

In one aspect, disclosed herein is a compound of Formula IV:

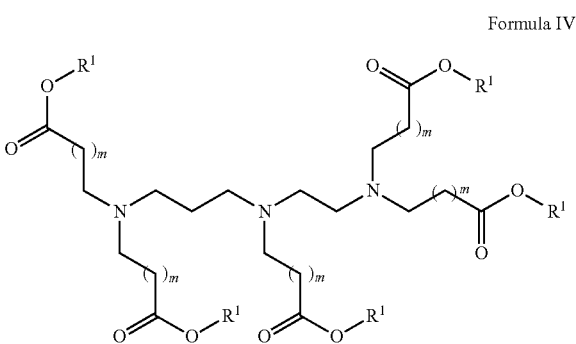

Formula IV and salts thereof; wherein
each $R^1$ is independently substituted or unsubstituted alkyl; or substituted or unsubstituted alkenyl; and
each m is independently 3, 4, 5, 6, 7, 8, 9, or 10.

In some embodiments, at least one $R^1$ is unsubstituted alkenyl. In some embodiments, at least one $R^1$ is substituted alkenyl. In some embodiments, at least one $R^1$ is

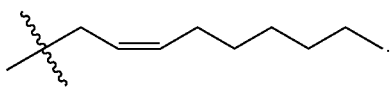 [SMILES: *C/C=C\CCCCCC]

In some embodiments, at least one $R^1$ is unsubstituted alkyl. In some embodiments, at least one $R^1$ is substituted alkyl. In some embodiments, $R^1$ is

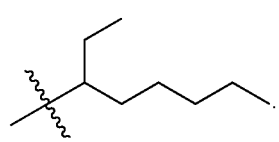 [SMILES: *C(CC)CCCCC]

In some embodiments, at least one m=7.
In some embodiments, at least one m=1. In some embodiments, at least one m=2. In some embodiments, at least one m=3. In some embodiments, at least one m=4. In some embodiments, at least one m=5. In some embodiments, at least one m=6. In some embodiments, at least one m=7. In some embodiments, at least one m=8. In some embodiments, at least one m=9. In some embodiments, at least one m=10.

In some embodiments, at least one $R^1$ is $C_6$-$C_{10}$ alkenyl. In some embodiments, at least one $R^1$ is $C_5$-$C_{15}$ alkenyl. In some embodiments, at least one $R^1$ is $C_9$ alkenyl. In some embodiments, at least one $R^1$ is a branched alkenyl. In some embodiments, at least one $R^1$ is an unbranched alkenyl.

In some embodiments, at least one $R^1$ is $C_6$-$C_{10}$ alkyl. In some embodiments, at least one $R^1$ is $C_5$-$C_{15}$ alkyl. In some embodiments, at least one $R^1$ is $C_8$ alkyl. In some embodiments, at least one $R^1$ is a branched alkyl.

In some embodiments, each $R^1$ is unsubstituted alkenyl. In some embodiments, each $R^1$ is substituted alkenyl. In some embodiments, each $R^1$ is In some embodiments, each $R^1$ is unsubstituted alkyl. In some embodiments, each $R^1$ is substituted alkyl. In some embodiments, each $R^1$ is In some embodiments, each m=7.

In some embodiments, each m=1. In some embodiments, each m=2. In some embodiments, each m=3. In some embodiments, each m=4. In some embodiments, each m=5. In some embodiments, each m=6. In some embodiments, each m=7. In some embodiments, each m=8. In some embodiments, each m=9. In some embodiments, each m=10.

In some embodiments, each $R^1$ is $C_6$-$C_{10}$ alkenyl. In some embodiments, each $R^1$ is $C_5$-$C_{15}$ alkenyl. In some embodiments, each $R^1$ is $C_9$ alkenyl. In some embodiments, each $R^1$ is a branched alkenyl. In some embodiments, each $R^1$ is an unbranched alkenyl.

In some embodiments, each $R^1$ is $C_6$-$C_{10}$ alkyl. In some embodiments, each $R^1$ is $C_5$-$C_{15}$ alkyl. In some embodiments, each $R^1$ is $C_8$ alkyl. In some embodiments, each $R^1$ is a branched alkyl.

In some embodiments, the disclosure provides compounds of Formula I, wherein:
each $R^1$ is independently substituted or unsubstituted alkyl; and
each m is independently 3, 4, 5, 6, 7, 8, 9, or 10.

In some embodiments, the disclosure provides compounds of Formula II, wherein:
each $R^1$ is independently substituted or unsubstituted alkyl; and
each m is independently 3, 4, 5, 6, 7, 8, 9, or 10.

In some embodiments, the disclosure provides compounds of Formula III, wherein:
each $R^1$ is independently substituted or unsubstituted alkyl; and
each m is independently 3, 4, 5, 6, 7, 8, 9, or 10.

In some embodiments, the disclosure provides compounds of Formula IV, wherein:
each $R^1$ is independently substituted or unsubstituted alkyl; and
each m is independently 3, 4, 5, 6, 7, 8, 9, or 10.

In some embodiments, the disclosure provides compounds of Formula I, wherein:
each $R^1$ is independently substituted or unsubstituted alkenyl; and
each m is independently 3, 4, 5, 6, 7, 8, 9, or 10.

In some embodiments, the disclosure provides compounds of Formula II, wherein:
each $R^1$ is independently substituted or unsubstituted alkenyl; and
each m is independently 3, 4, 5, 6, 7, 8, 9, or 10.

In some embodiments, the disclosure provides compounds of Formula III, wherein:
each $R^1$ is independently substituted or unsubstituted alkenyl; and
each m is independently 3, 4, 5, 6, 7, 8, 9, or 10.

In some embodiments, the disclosure provides compounds of Formula IV, wherein:
each $R^1$ is independently substituted or unsubstituted alkenyl; and
each m is independently 3, 4, 5, 6, 7, 8, 9, or 10.

In some embodiments, the disclosure provides compounds of Formula I, wherein:
each $R^1$ is independently substituted or unsubstituted alkyl; and
each m is independently 7.

In some embodiments, the disclosure provides compounds of Formula II, wherein:
each $R^1$ is independently substituted or unsubstituted alkyl; and
each m is independently 7.

In some embodiments, the disclosure provides compounds of Formula III, wherein:
each $R^1$ is independently substituted or unsubstituted alkyl; and
each m is independently 7.

In some embodiments, the disclosure provides compounds of Formula IV, wherein:
each $R^1$ is independently substituted or unsubstituted alkyl; and
each m is independently 7.

In some embodiments, the disclosure provides compounds of Formula I, wherein:
each $R^1$ is independently substituted or unsubstituted alkenyl; and
each m is independently 7.

In some embodiments, the disclosure provides compounds of Formula II, wherein:
each $R^1$ is independently substituted or unsubstituted alkenyl; and
each m is independently 7.

In some embodiments, the disclosure provides compounds of Formula III, wherein:
each $R^1$ is independently substituted or unsubstituted alkenyl; and
each m is independently 7.

In some embodiments, the disclosure provides compounds of Formula IV, wherein:
each $R^1$ is independently substituted or unsubstituted alkenyl; and
each m is independently 7.

In some embodiments, the disclosure provides compounds of Formula I, wherein:
all instances of $R^1$ are substituted or unsubstituted alkyl; and
all instances of m are 3, 4, 5, 6, 7, 8, 9, or 10.

In some embodiments, the disclosure provides compounds of Formula II, wherein:
all instances of $R^1$ are substituted or unsubstituted alkyl; and
all instances of m are 3, 4, 5, 6, 7, 8, 9, or 10.

In some embodiments, the disclosure provides compounds of Formula III, wherein:
all instances of $R^1$ are substituted or unsubstituted alkyl; and
all instances of m are 3, 4, 5, 6, 7, 8, 9, or 10.

In some embodiments, the disclosure provides compounds of Formula IV, wherein:
all instances of $R^1$ are substituted or unsubstituted alkyl; and
all instances of m are 3, 4, 5, 6, 7, 8, 9, or 10.

In some embodiments, the disclosure provides compounds of Formula I, wherein:
all instances of $R^1$ are substituted or unsubstituted alkenyl; and
all instances of m are 3, 4, 5, 6, 7, 8, 9, or 10.

In some embodiments, the disclosure provides compounds of Formula II, wherein:
all instances of $R^1$ are substituted or unsubstituted alkenyl; and
all instances of m are 3, 4, 5, 6, 7, 8, 9, or 10.

In some embodiments, the disclosure provides compounds of Formula III, wherein:
all instances of $R^1$ are substituted or unsubstituted alkenyl; and
all instances of m are 3, 4, 5, 6, 7, 8, 9, or 10.

In some embodiments, the disclosure provides compounds of Formula IV, wherein:
all instances of $R^1$ are substituted or unsubstituted alkenyl; and
all instances of m are 3, 4, 5, 6, 7, 8, 9, or 10.

In some embodiments, the disclosure provides compounds of Formula I, wherein:
all instances of $R^1$ are substituted or unsubstituted alkyl; and
all instances of m are 7.

In some embodiments, the disclosure provides compounds of Formula II, wherein:
all instances of $R^1$ are substituted or unsubstituted alkyl; and
all instances of m are 7.

In some embodiments, the disclosure provides compounds of Formula III, wherein:
all instances of $R^1$ are substituted or unsubstituted alkyl; and
all instances of m are 7.

In some embodiments, the disclosure provides compounds of Formula IV, wherein:
all instances of $R^1$ are substituted or unsubstituted alkyl; and
all instances of m are 7.

In some embodiments, the disclosure provides compounds of Formula I, wherein:
all instances of $R^1$ are substituted or unsubstituted alkenyl; and
all instances of m are 7.

In some embodiments, the disclosure provides compounds of Formula II, wherein:
all instances of $R^1$ are substituted or unsubstituted alkenyl; and
all instances of m are 7.

In some embodiments, the disclosure provides compounds of Formula III, wherein:
all instances of $R^1$ are substituted or unsubstituted alkenyl; and
all instances of m are 7.

In some embodiments, the disclosure provides compounds of Formula IV, wherein:
all instances of $R^1$ are substituted or unsubstituted alkenyl; and
all instances of m are 7.

In one embodiment, the compound is:

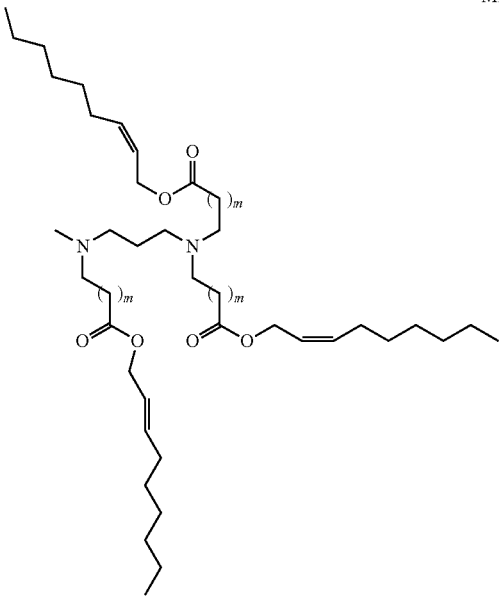

MPA-A and salts thereof, wherein each m=7.

In one embodiment, the compound is:

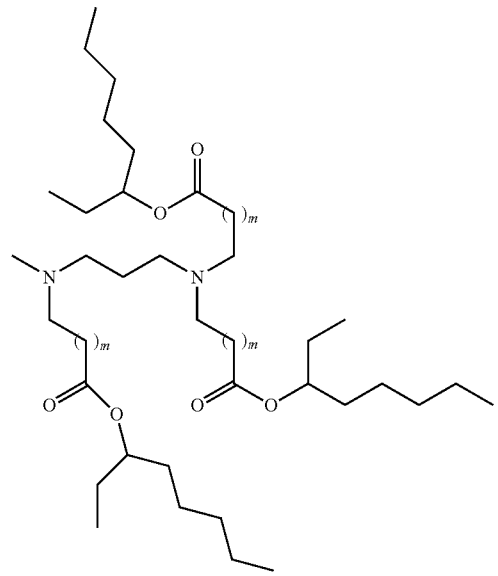

MPA-Ab and salts thereof, wherein each m=7.

In another aspect, disclosed herein is a composition comprising:
a compound of Formula I, II, III, or IV; and
an agent.

In another aspect, disclosed herein is a composition comprising:
a compound of Formula I;

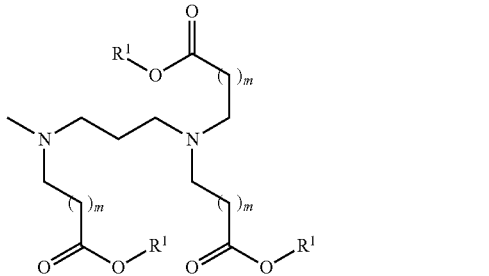

Formula I and salts thereof; wherein
each $R^1$ is independently substituted or unsubstituted alkyl; or substituted or unsubstituted alkenyl;
each m is independently 3, 4, 5, 6, 7, 8, 9, or 10; and
an agent.

In some embodiments, at least one $R^1$ is unsubstituted alkenyl. In some embodiments, at least one $R^1$ is

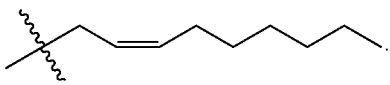 [SMILES: *C/C=C\CCCCCC]

In some embodiments, at least one $R^1$ is unsubstituted alkyl. In some embodiments, $R^1$ is

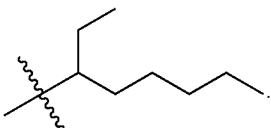 [SMILES: *C(CC)CCCCC]

In some embodiments, at least one m=7.
In some embodiments, at least one $R^1$ is $C_6$-$C_{10}$ alkenyl. In some embodiments, at least one $R^1$ is a branched alkenyl. In some embodiments, at least one $R^1$ is $C_6$-$C_{10}$ alkyl. In some embodiments, at least one $R^1$ is a branched alkyl.

In some embodiments, each $R^1$ is unsubstituted alkenyl. In some embodiments, each $R^1$ is

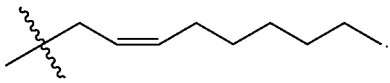

In some embodiments, each $R^1$ is unsubstituted alkyl. In some embodiments, each $R^1$ is

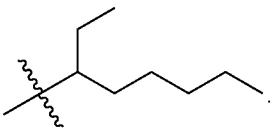 [SMILES: *C(CC)CCCCC]

In some embodiments, each m=7. In some embodiments, each $R^1$ is $C_6$-$C_{10}$ alkenyl. In some embodiments, each $R^1$ is a branched alkenyl. In some embodiments, each $R^1$ is $C_6$-$C_{10}$ alkyl. In some embodiments, each $R^1$ is a branched alkyl.

In some embodiments, the agent is a polynucleotide. In some embodiments, the agent is an RNA. In some embodiments, the agent is an mRNA.

Lipid-Like Nanoparticles (LLNs)

In one aspect, the disclosure provides a nanoparticle comprising:
a compound of Formula I, II, III, or IV;
a non-cationic lipid;
a polyethylene glycol-lipid; and
a sterol.

The various compounds of Formula I, II, III, or IV are described in the Compounds section above. In some embodiments, the nanoparticle comprises a compound of Formula I, II, III, or IV in a molar ratio of about 10% to about 40%. In some embodiments, the nanoparticle comprises a compound of Formula I, II, III, or IV in a molar ratio of about 10%, about 15%, about 20%, about 25%, about 30%, about 35%, or about 40%. In one embodiment, the nanoparticle comprises a compound of Formula I, II, III, or IV in a molar ratio of about 20%.

In some embodiments, the nanoparticle comprises a non-cationic lipid. In some embodiments, the non-cationic lipid interacts with the lipids as a helper lipid. In some embodiments, the non-cationic lipid can include, but is not limited to, 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), DPPC (1,2-dipalmitoyl-sn-glycero-3-phosphocholine), 1,2-dioleyl-sn-glycero-3-phosphotidylcholine (DOPC), 1,2-dipalmitoyl-sn-glycero-3-phosphoethanolamine (DPPE), 1,2-dimyristoyl-sn-glycero-3-phosphoethanolamine (DMPE), 1,2-dioleoyl-5/7-glycero-3-phospho-(1'-rac-glycerol) (DOPG), or combinations thereof. In one embodiment, the non-cationic lipid is 1,2-dioleoyl-sn-glycero-3-phosphoethanolamine (DOPE). In one embodiment, the non-cationic lipid is 1-palmitoyl-2-oleoyl-sn-glycero-3-phosphoethanolamine (POPE), In one embodiment, the non-cationic lipid is 1,2-distearoyl-sn-glycero-3-phosphocholine (DSPC). In one embodiment, the non-cationic lipid is 1-stearoyl-2-oleoyl-sn-glycero-3-phosphoethanolamine (SOPE).

In some embodiments, the nanoparticle comprises a non-cationic lipid in a molar ratio of about 10% to about 40%. In some embodiments, the nanoparticle comprises a non-cationic lipid in a molar ratio of about 10%, about 15%, about 20%, about 25%, about 30%, about 35%, or about 40%. In one embodiment, the nanoparticle comprises a non-cationic lipid in a molar ratio of about 30%.

In some embodiments, the nanoparticle includes a polyethylene glycol-lipid (PEG-lipid). PEG-lipid is incorporated to form a hydrophilic outer layer and stabilize the particles. Nonlimiting examples of polyethylene glycol-lipids include PEG-modified lipids such as PEG-modified phosphatidylethanolamines, PEG-modified phosphatidic acids, PEG-modified ceramides, PEG-modified dialkylamines, PEG-modified diacylglycerols, and PEG-modified dialkylglycerols. Representative polyethylene glycol-lipids include DMG-PEG, DLPE-PEGs, DMPE-PEGs, DPPC-PEGs, and DSPE-PEGs. In one embodiment, the polyethylene glycol-lipid is 1,2-dimyristoyl-sn-glycerol, methoxypolyethylene glycol (DMG-PEG). In one embodiment, the polyethylene glycol-lipid is 1,2-dimyristoyl-sn-glycerol, methoxypolyethylene glycol-2000 (DMG-PEG2000). DMG-PEGXXXX means 1,2-dimyristoyl-sn-glycerol, methoxypolyethylene glycol-XXXX, wherein XXXX signifies the molecular weight of the polyethylene glycol moiety, e.g. DMG-PEG2000 or DMG-PEG5000.

In some embodiments, the nanoparticle comprises a polyethylene glycol-lipid in a molar ratio of about 0% to about 5%. In some embodiments, the nanoparticle comprises a polyethylene glycol-lipid in a molar ratio of about 0%, about 0.25%, about 0.5%, about 0.75%, about 1%, about 1.5%, about 2%, about 3%, about 4%, or about 5%. In one embodiment, the nanoparticle comprises a polyethylene glycol-lipid in a molar ratio of about 0.75%.

In some embodiments, the nanoparticle includes a sterol. Sterols are well known to those skilled in the art and generally refers to those compounds having a perhydrocyclopentanophenanthrene ring system and having one or more OH substituents. Examples of sterols include, but are not limited to, cholesterol, campesterol, ergosterol, sitosterol, and the like.

In some embodiments, the sterol is selected from a cholesterol-based lipids. In some embodiments, the one or more cholesterol-based lipids are selected from cholesterol, PEGylated cholesterol, DC-Choi (N,N-dimethyl-N-ethyl carboxamidocholesterol), 1,4-bis(3-N-oleylamino-propyl) piperazine, or combinations thereof.

The sterol can be used to tune the particle permeability and fluidity base on its function in cell membranes. In one embodiment, the sterol is cholesterol.

In some embodiments, the nanoparticle comprises a sterol in a molar ratio of about 25% to about 50%. In some embodiments, the nanoparticle comprises a sterol in a molar ratio of about 25%, about 30%, about 35%, about 40%, about 45%, or about 50%. In one embodiment, the nanoparticle comprises a sterol in a molar ratio of about 40%.

In one embodiment, the disclosure provides a nanoparticle comprising:
a compound of Formula I, II, III, or IV at a molar ratio of about 20%;
a non-cationic lipid at a molar ratio of about 30%;
a polyethylene glycol-lipid at a molar ratio of about 0.75%; and
a sterol at a molar ratio of about 40%.

In one embodiment, the disclosure provides a nanoparticle comprising:
a compound of Formula I, II, III, or IV;
1,2-dioleoyl-sn-glycero-3-phosphoethanolamine (DOPE);
1,2-dimyristoyl-sn-glycerol, methoxypolyethylene glycol (DMG-PEG$_{2000}$); and
cholesterol.

In a further aspect, disclosed herein is a nanoparticle comprising:
a compound of Formula I;

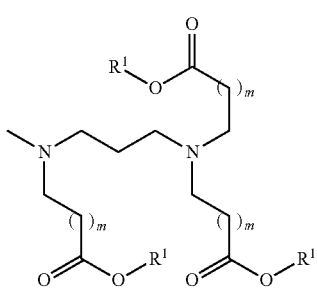

Formula I and salts thereof wherein
each $R^1$ is independently substituted or unsubstituted alkyl; or substituted or unsubstituted alkenyl;
each m is independently 3, 4, 5, 6, 7, 8, 9, or 10;
a non-cationic lipid;
a polyethylene glycol-lipid; and
a sterol.

In some embodiments, the compound of Formula I is:

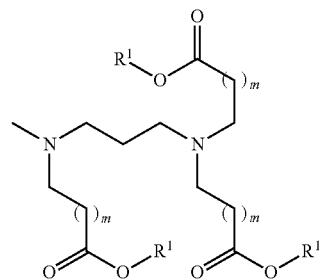

and salts thereof, wherein each m=7; and
each $R^1$ is selected from

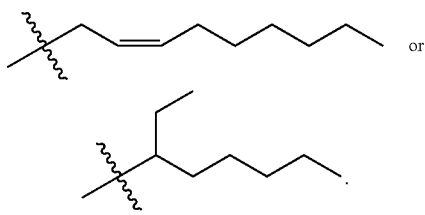

In one embodiment, the disclosure provides a nanoparticle comprising:
compound MPA-A;
1,2-dioleoyl-sn-glycero-3-phosphoethanolamine (DOPE);
1,2-dimyristoyl-sn-glycerol, methoxypolyethylene glycol (DMG-PEG$_{2000}$); and
cholesterol.

In one embodiment, the disclosure provides a nanoparticle comprising:
compound MPA-Ab;
1,2-dioleoyl-sn-glycero-3-phosphoethanolamine (DOPE);
1,2-dimyristoyl-sn-glycerol, methoxypolyethylene glycol (DMG-PEG2000); and
cholesterol.

In one embodiment, the nanoparticle further comprises an agent. In one embodiment, the nanoparticle further comprises a therapeutic agent. In one embodiment, the nanoparticle further comprises a diagnostic agent.

The agents delivered into cells can be a polynucleotide. Polynucleotides or oligonucleotides that can be introduced according to the methods herein include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA.

The term "nanoparticle" and "lipid-like nanoparticle (LLN)" are used interchangeably in the present disclosure.

Compositions

Compositions, as described herein, comprising an active compound and an excipient of some sort may be useful in a variety of medical and non-medical applications. For example, pharmaceutical compositions comprising an active compound and an excipient may be useful in the delivery of an effective amount of an agent to a subject in need thereof. Nutraceutical compositions comprising an active compound and an excipient may be useful in the delivery of an effective amount of a nutraceutical, e.g., a dietary supplement, to a subject in need thereof. Cosmetic compositions comprising an active compound and an excipient may be formulated as a cream, ointment, balm, paste, film, or liquid, etc., and may be useful in the application of make-up, hair products, and materials useful for personal hygiene, etc. Compositions comprising an active compound and an excipient may be useful for non-medical applications, e.g., such as an emulsion or emulsifier, useful, for example, as a food component, for extinguishing fires, for disinfecting surfaces, for oil cleanup, etc.

In certain embodiments, the composition further comprises an agent, as described herein. For example, in certain embodiments, the agent is a small molecule, organometallic compound, nucleic acid, protein, peptide, polynucleotide, metal, targeting agent, an isotopically labeled chemical compound, drug, vaccine, immunological agent, or an agent useful in bioprocessing. In certain embodiments, the agent is a polynucleotide. In certain embodiments, the polynucleotide is DNA or RNA. In certain embodiments, the RNA is RNAi, dsRNA, siRNA, shRNA, miRNA, or antisense RNA. In certain embodiments, the polynucleotide and the one or more active compounds are not covalently attached.

In one aspect, the disclosure provides a composition comprising:
a compound of Formula I, II, III, or IV; and
an agent.

In one aspect, the disclosure provides a composition comprising:
a nanoparticle, comprising a compound of Formula I, II, III, or IV; and
an agent.

In some embodiments, the composition further comprises a non-cationic lipid (helper lipid). In some embodiments, the composition further comprises a polyethylene glycol-lipid (PEG modified lipid). In some embodiments, the composition further comprises a sterol.

In some embodiments, the composition further comprises a non-cationic lipid (helper lipid); and/or a polyethylene glycol-lipid (PEG modified lipid); and/or a sterol.

"Excipients" include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in formulation and/or manufacture can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21st Edition (Lippincott Williams & Wilkins, 2005).

Exemplary excipients include, but are not limited to, any non-toxic, inert solid, semi-solid or liquid filler, diluent, encapsulating material or formulation auxiliary of any type. Some examples of materials which can serve as excipients include, but are not limited to, sugars such as lactose, glucose, and sucrose; starches such as corn starch and potato starch; cellulose and its derivatives such as sodium carboxymethyl cellulose, ethyl cellulose, and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols such as propylene glycol; esters such as ethyl oleate and ethyl laurate; agar; detergents such as Tween 80; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. As would be appreciated by one of skill in this art, the excipients may be chosen based on what the composition is useful for. For example, with a pharmaceutical composition or cosmetic composition, the choice of the excipient will depend on the route of administration, the agent being delivered, time course of delivery of the agent, etc., and can be administered to humans and/or to animals, orally, rectally, parenterally, intracisternally, intravaginally, intranasally, intraperitoneally, topically (as by powders, creams, ointments, or drops), bucally, or as an oral or nasal spray.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g.

polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Additionally, the composition may further comprise a polymer. Exemplary polymers contemplated herein include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC) and its various salts, including, e.g., the sodium salt, hydroxyethylcarboxymethylcellulose (HECMC) and its various salts, carboxymethylhydroxyethylcellulose (CMHEC) and its various salts, other polysaccharides and polysaccharide derivatives such as starch, dextran, dextran derivatives, chitosan, and alginic acid and its various salts, carageenan, various gums, including xanthan gum, guar gum, gum arabic, gum karaya, gum ghatti, konjac and gum tragacanth, glycosaminoglycans and proteoglycans such as hyaluronic acid and its salts, proteins such as gelatin, collagen, albumin, and fibrin, other polymers, for example, polyhydroxyacids such as polylactide, polyglycolide, polyl(lactide-co-glycolide) and poly(.epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), and a Pluronic polymer, polyoxyethylene (polyethylene glycol), polyanhydrides, polyvinylalchol, polyethyleneamine and polypyrridine, polyethylene glycol (PEG) polymers, such as PEGylated lipids (e.g., PEG-stearate, 1,2-Distearoyl-sn-glycero-3-Phosphoethanolamine-N-[Methoxy(Polyethylene glycol)-1000], 1,2-Distearoyl-sn-glycero-3-Phosphoethanolamine-N-[Methoxy(Polyethylene glycol)-2000], and 1,2-Distearoyl-sn-glycero-3-Phosphoethanolamine-N-[Methoxy(Polyethylene glycol)-5000]), copolymers and salts thereof.

Additionally, the composition may further comprise an emulsifying agent. Exemplary emulsifying agents include, but are not limited to, a polyethylene glycol (PEG), a polypropylene glycol, a polyvinyl alcohol, a poly-N-vinyl pyrrolidone and copolymers thereof, poloxamer nonionic surfactants, neutral water-soluble polysaccharides (e.g., dextran, Ficoll, celluloses), non-cationic poly(meth)acrylates, non-cationic polyacrylates, such as poly(meth)acrylic acid, and esters amide and hydroxyalkyl amides thereof, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [ Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof. In certain embodiments, the emulsifying agent is cholesterol.

Liquid compositions include emulsions, microemulsions, solutions, suspensions, syrups, and elixirs. In addition to the active compound, the liquid composition may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable compositions, for example, injectable aqueous or oleaginous suspensions may be formulated according to the known art using suitable dispersing or wetting agents and suspending agents. The sterile injectable preparation may also be a injectable solution, suspension, or emulsion in a nontoxic parenterally acceptable diluent or solvent, for example, as a solution in 1,3-butanediol. Among the acceptable vehicles and solvents for pharmaceutical or cosmetic compositions that may be employed are water, Ringer's solution, U.S.P. and isotonic sodium chloride solution. In addition, sterile, fixed oils are conventionally employed as a solvent or suspending medium. Any bland fixed oil can be employed including synthetic mono- or diglycerides. In addition, fatty acids such as oleic acid are used in the preparation of injectables. In certain embodiments, the particles are suspended in a carrier fluid comprising 1% (w/v) sodium carboxymethyl cellulose and 0.1% (v/v) Tween 80. The injectable composition can be sterilized, for example, by filtration through a bacteria-retaining filter, or by incorporating sterilizing agents in the form of sterile solid compositions which can be dissolved or dispersed in sterile water or other sterile injectable medium prior to use.

Compositions for rectal or vaginal administration may be in the form of suppositories which can be prepared by mixing the particles with suitable non-irritating excipients or carriers such as cocoa butter, polyethylene glycol, or a suppository wax which are solid at ambient temperature but liquid at body temperature and therefore melt in the rectum or vaginal cavity and release the particles.

Solid compositions include capsules, tablets, pills, powders, and granules. In such solid compositions, the particles are mixed with at least one excipient and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets, and pills, the dosage form may also comprise buffering agents. Solid compositions of a similar type may also be employed as fillers in soft and hard-filled gelatin capsules using such excipients as lactose or milk sugar as well as high molecular weight polyethylene glycols and the like.

Tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

Compositions for topical or transdermal administration include ointments, pastes, creams, lotions, gels, powders, solutions, sprays, inhalants, or patches. The active compound is admixed with an excipient and any needed preservatives or buffers as may be required. Ophthalmic formulation, ear drops, and eye drops are also contemplated as being within the scope of this invention.

The ointments, pastes, creams, and gels may contain, in addition to the active compound, excipients such as animal and vegetable fats, oils, waxes, paraffins, starch, tragacanth, cellulose derivatives, polyethylene glycols, silicones, bentonites, silicic acid, talc, and zinc oxide, or mixtures thereof.

Powders and sprays can contain, in addition to the active compound, excipients such as lactose, talc, silicic acid, aluminum hydroxide, calcium silicates, and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the nanoparticles in a proper medium. Absorption enhancers can also be used to increase the flux of the compound across the skin. The rate can be controlled by either providing a rate controlling membrane or by dispersing the particles in a polymer matrix or gel.

Agents

Agents to be delivered by the systems described herein may be therapeutic, diagnostic, or prophylactic agents. Any chemical compound to be administered to a subject may be delivered using the particles or nanoparticles described herein. The agent may be an organic molecule (e.g., a therapeutic agent, a drug), inorganic molecule, nucleic acid, protein, amino acid, peptide, polypeptide, polynucleotide, targeting agent, isotopically labeled organic or inorganic molecule, vaccine, immunological agent, etc.

In certain embodiments, the agents are organic molecules with pharmaceutical activity, e.g., a drug. In certain embodiments, the drug is an antibiotic, anti-viral agent, anesthetic, steroidal agent, anti-inflammatory agent, anti-neoplastic agent, anti-cancer agent, antigen, vaccine, antibody, decongestant, antihypertensive, sedative, birth control agent, progestational agent, anti-cholinergic, analgesic, anti-depressant, anti-psychotic, f3-adrenergic blocking agent, diuretic, cardiovascular active agent, vasoactive agent, non-steroidal anti-inflammatory agent, nutritional agent, etc.

In certain embodiments of the present disclosure, the agent to be delivered may be a mixture of agents.

Diagnostic agents include gases; metals; commercially available imaging agents used in positron emissions tomography (PET), computer assisted tomography (CAT), single photon emission computerized tomography, x-ray, fluoroscopy, and magnetic resonance imaging (MRI); and contrast agents. Examples of suitable materials for use as contrast agents in Mill include gadolinium chelates, as well as iron, magnesium, manganese, copper, and chromium. Examples of materials useful for CAT and x-ray imaging include iodine-based materials.

Therapeutic and prophylactic agents include, but are not limited to, antibiotics, nutritional supplements, and vaccines. Vaccines may comprise isolated proteins or peptides, inactivated organisms and viruses, dead organisms and viruses, genetically altered organisms or viruses, and cell extracts. Therapeutic and prophylactic agents may be combined with interleukins, interferon, cytokines, and adjuvants such as cholera toxin, alum, Freund's adjuvant, etc. Prophylactic agents include antigens of such bacterial organisms as *Streptococccus pneumoniae, Haemophilus influenzae, Staphylococcus aureus, Streptococcus pyrogenes, Corynebacterium diphtherias, Listeria monocytogenes, Bacillus anthracis, Clostridium tetani, Clostridium botulinum, Clostridium perfringens, Neisseria meningitidis, Neisseria gonorrhoeae, Streptococcus mutans, Pseudomonas aeruginosa, Salmonella typhi, Haemophilus parainfluenzae, Bordetella pertussis, Francisella tularensis, Yersinia pestis, Vibrio cholerae, Legionella pneumophila, Mycobacterium tuberculosis, Mycobacterium leprae, Treponema pallidum, Leptospirosis interrogans, Borrelia burgdorferi, Camphylobacter jejuni*, and the like; antigens of such viruses as smallpox, influenza A and B, respiratory syncytial virus, parainfluenza, measles, HIV, varicella-zoster, herpes simplex 1 and 2, cytomegalovirus, Epstein-Barr virus, rotavirus, rhinovirus, adenovirus, papillomavirus, poliovirus, mumps, rabies, rubella, coxsackieviruses, equine encephalitis, Japanese encephalitis, yellow fever, Rift Valley fever, hepatitis A, B, C, D, and E virus, and the like; antigens of fungal, protozoan, and parasitic organisms such as *Cryptococcus neoformans, Histoplasma capsulatum, Candida albicans, Candida tropicalis, Nocardia asteroides, Rickettsia ricketsii, Rickettsia typhi, Mycoplasma pneumoniae, Chlamydial psittaci, Chlamydial trachomatis, Plasmodium falciparum, Trypanosoma brucei, Entamoeba histolytica, Toxoplasma gondii, Trichomonas vaginalis, Schistosoma mansoni*, and the like. These antigens may be in the form of whole killed organisms, peptides, proteins, glycoproteins, carbohydrates, or combinations thereof.

Genetic Diseases and Methods of Treatment

It is estimated that over 10,000 human diseases are caused by genetic disorders, which are abnormalities in genes or chromosomes. See, e.g., McClellan, J. and M. C. King, *Genetic heterogeneity in human disease*. Cell. 141(2): p. 210-7; Leachman, S. A., et al., *Therapeutic siRNAs for dominant genetic skin disorders including pachyonychia congenita*. J Dermatol Sci, 2008. 51(3): p. 151-7. Many of these diseases are fatal, such as cancer, severe hypercholesterolemia, and familial amyloidotic polyneuropathy. See, e.g., Frank-Kamenetsky, M., et al., *Therapeutic RNA1 targeting PCSK9 acutely lowers plasma cholesterol in rodents and LDL cholesterol in nonhuman primates*. Proc Natl Acad Sci USA, 2008. 105(33): p. 11915-20; Coelho, T., *Familial amyloid polyneuropathy: new developments in genetics and treatment*. Curr Opin Neurol, 1996. 9(5): p. 355-9. Since the discovery of gene expression silencing via RNA interference (RNAi) by Fire and Mello (Fire, A., et al., *Potent and specific genetic interference by double-stranded RNA in Caenorhabditis elegans*. Nature, 1998. 391(6669): p. 806-11), there has been extensive effort toward developing therapeutic Applications for RNAi in humans. See, e.g., Davis, M. E., *The first targeted delivery of siRNA in humans via a self-assembling, cyclodextrin polymer-based nanoparticle: from concept to clinic*. Mol Pharm, 2009. 6(3): p. 659-68; Whitehead, K. A., R. Langer, and D. G. Anderson, *Knocking down barriers: advances in siRNA delivery*. Nat. Rev. Drug Discovery, 2009. 8(2): p. 129-138; Tan, S. J., et al., *Engineering Nanocarriers for siRNA Delivery*. Small. 7(7): p. 841-56; Castanotto, D. and J. J. Rossi, *The promises and pitfalls of RNA-interference-based therapeutics*. Nature, 2009. 457(7228): p. 426-33; Chen, Y. and L. Huang, *Tumor-targeted delivery of siRNA by non-viral vector: safe and effective cancer therapy.* Expert Opin Drug Deliv, 2008. 5(12): p. 1301-11; Weinstein, S, and D. Peer, *RNAi nanomedicines: challenges and opportunities within the immune system.* Nanotechnology. 21(23): p. 232001; Fenske, D. B. and P. R. Cullis, *Liposomal nanomedicines.* Expert Opin Drug Deliv, 2008. 5(1): p. 25-44; and Thiel, K. W. and P. H. Giangrande, *Therapeutic Applications of DNA and RNA aptamers.* Oligonucleotides, 2009. 19(3): p. 209-22. Currently, there are more than 20 clinical trials ongoing or completed involving siRNA therapeutics, which have shown promising results for the treatment of various diseases. See, e.g., Burnett, J. C., J. J. Rossi, and K. Tiemann, *Current progress of siRNA/shRNA therapeutics in clinical trials.* Biotechnol J. 6(9): p. 1130-46. However, the efficient and safe delivery of siRNA is still a key challenge in the development of siRNA therapeutics. See, e.g., Juliano, R., et al., *Biological barriers to therapy with antisense and siRNA oligonucleotides.* Mol Pharm, 2009. 6(3): p. 686-95.

Thus, in another aspect, provided are methods of using active compounds, e.g., for the treatment of a disease, disorder or condition from which a subject suffers. It is contemplated that active compounds will be useful in the treatment of a variety of diseases, disorders, or conditions, especially a system for delivering agents useful in the treatment of that particular disease, disorder, or condition. "Disease," "disorder," and "condition" are used interchangeably herein. In certain embodiments, the disease, disorder or condition from which a subject suffers is caused by an abnormality in a gene or chromosome of the subject.

For example, in one embodiment, provided is a method of treating disease, disorder, or condition from which a subject suffers, comprising administering to a subject in need thereof an effective amount of a composition comprising an active compound, or salt thereof. Exemplary disease, disorder, or conditions contemplated include, but are not limited to, proliferative disorders, inflammatory disorders, autoimmune disorders, painful conditions, liver diseases, and amyloid neuropathies.

As used herein, an "active ingredient" is any agent which elicits the desired biological response. For example, the active compound may be the active ingredient in the composition. Other agents, e.g., therapeutic agents, as described herein may also be classified as an active ingredient. In certain embodiments, the composition further comprises, in addition to the active compound, a therapeutic agent useful in treating the disease, disorder, or condition. In certain embodiments, the active compound encapsulates the other (therapeutic) agent. In certain embodiments, the active compound and the other (therapeutic) agent form a particle (e.g., a nanoparticle).

In certain embodiments, the condition is a proliferative disorder and, in certain embodiments, the composition further includes an anti-cancer agent. Exemplary proliferative diseases include, but are not limited to, tumors, benign neoplasms, pre-malignant neoplasms (carcinoma in situ), and malignant neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenstrom's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

Anti-cancer agents encompass biotherapeutic anti-cancer agents as well as chemotherapeutic agents.

Exemplary biotherapeutic anti-cancer agents include, but are not limited to, interferons, cytokines (e.g., tumor necrosis factor, interferon α, interferon γ), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)).

Exemplary chemotherapeutic agents include, but are not limited to, anti-estrogens (e.g. tamoxifen, raloxifene, and megestrol), LHRH agonists (e.g. goscrelin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetrexate, edatrexate), IMP dehydrogenase inhibitors (e.g. mycophenolic acid, tiazofurin, ribavirin, and EICAR), ribonucleotide reductase inhibitors (e.g. hydroxyurea and deferoxamine), uracil analogs (e.g. 5-fluorouracil (5-FU), floxuridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. staurosporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalidomide, lenalidomide, tyrosine kinase inhibitors (e.g., axitinib (AG013736), bosutinib (SKI-606), cediranib (RECENTIN™, AZD2171), dasatinib (SPRYCEL®, BMS-354825), erlotinib (TARCEVA®), gefitinib (IRESSA®), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLADIA®), vandetanib (ZACTIMA®, ZD6474), vatalanib (PTK787, PTK/ZK), trastuzumab (HERCEPTIN®), bevacizumab (AVASTIN®), rituximab (RITUXAN®), cetuximab (ERBITUX®), panitumumab (VECTIBIX®), ranibizumab (Lucentis®), nilotinib (TASIGNA®), sorafenib (NEXAVAR®), everolimus (AFINITOR®), alemtuzumab (CAMPATH®), gemtuzumab ozogamicin (MYLOTARG®), temsirolimus (TORISEL®), ENMD-2076, PCI-32765, AC220, dovitinib lactate (TKI258, CHIR-258), BMW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bortezomib (VELCADE)), mTOR inhibitors (e.g., rapamycin, temsirolimus (CCI-779), everolimus (RAD-001), ridaforolimus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genetech), SF1126 (Semafoe) and OSI-027 (OSI)), oblimersen, gemcitabine, caminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leurosine, chlorambucil, trabectedin, procarbazine, discodermolide, caminomycin, aminopterin, and hexamethyl melamine.

In certain embodiments, the condition is an inflammatory disorder and, in certain embodiments, the composition further includes an anti-inflammatory agent. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition is an autoimmune disorder and, in certain embodiments, the composition further includes an immunomodulatory agent. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as non-ulcerative dyspepsia (NUD) and non-cardiac chest pain (NCCP, including costo-chondritis)).

In certain embodiments, the condition is a painful condition and, in certain embodiments, the composition further includes an analgesic agent. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with drawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is inflammatory pain. In certain embodiments, the painful condition (e.g., inflammatory pain) is associated with an inflammatory disorder and/or an autoimmune disorder.

In certain embodiments, the condition is a liver disease and, in certain embodiments, the composition further includes an agent useful in treating liver disease. Exemplary liver diseases include, but are not limited to, drug-induced liver injury (e.g., acetaminophen-induced liver injury), hepatitis (e.g., chronic hepatitis, viral hepatitis, alcohol-induced hepatitis, autoimmune hepatitis, steatohepatitis), non-alcoholic fatty liver disease, alcohol-induced liver disease (e.g., alcoholic fatty liver, alcoholic hepatitis, alcohol-related cirrhosis), hypercholesterolemia (e.g., severe hypercholesterolemia), transthyretin-related hereditary amyloidosis, liver cirrhosis, liver cancer, primary biliary cirrhosis, cholestatis, cystic disease of the liver, and primary sclerosing cholangitis. In certain embodiments the liver disease is associated with inflammation.

In certain embodiments, the condition is a familial amyloid neuropathy and, in certain embodiments, the composition further includes an agent useful in a familial amyloid neuropathy.

The active ingredient may be administered in such amounts, time, and route deemed necessary in order to achieve the desired result. The exact amount of the active ingredient will vary from subject to subject, depending on the species, age, and general condition of the subject, the severity of the infection, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The active ingredient may be administered by any route. In some embodiments, the active ingredient is administered via a variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the active ingredient (e.g., its stability in the environment of the gastrointestinal tract), the condition of the subject (e.g., whether the subject is able to tolerate oral administration), etc.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Methods

In one aspect, provided herein is a method for the delivery of an agent (for example, a polynucleotide) into a cell comprising;
introducing into the cell a composition comprising;
i) a nanoparticle, comprising;
    a compound of Formula I, II, III, or IV;
    a non-cationic lipid;
    a polyethylene glycol-lipid;
    a sterol; and
ii) an agent.

In one aspect, disclosed herein is a method for the delivery of an agent into a cell comprising;
introducing into the cell a composition comprising;
a nanoparticle comprising;
    a compound of Formula I;

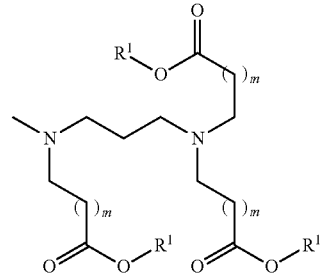

Formula I and salts thereof; wherein
each $R^1$ is independently substituted or unsubstituted alkyl; or substituted or unsubstituted alkenyl;
each m is independently 3, 4, 5, 6, 7, 8, 9, or 10;
a non-cationic lipid;
a polyethylene glycol-lipid;
a sterol; and
an agent.

In some embodiments, the agent is a polynucleotide. In some embodiments, the agent is an RNA. In some embodiments, the agent is an mRNA. In some embodiments, the agent is a therapeutic agent, diagnostic agent, or prophylactic agent.

In some embodiments, provided herein are methods for the delivery of polynucleotides. In some embodiments, provided herein are methods for the delivery of polynucleotides (for example, mRNA) to correct a mutation in a genome. For example, mRNAs can be delivered to correct mutations that cause hemophilia (due to mutations in the genes encoding Factor VIII (F8; hemophilia A) or Factor IX (F9; hemoglobin B).

In some embodiments, the compound of Formula I is:

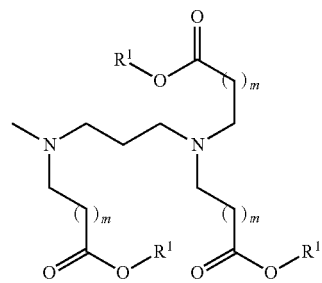

and salts thereof, wherein each m=7; and
each $R^1$ is selected from

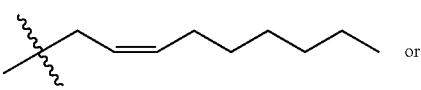

or

-continued

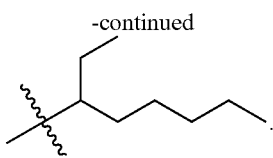

In some embodiments, the phosphatidylethanolamine lipid is selected from 1,2-dioleoyl-sn-glycero-3-phosphoethanolamine (DOPE), 1-palmitoyl-2-oleoyl-sn-glycero-3-phosphoethanolamine (POPE), 1,2-distearoyl-sn-glycero-3-phosphocholine (DSPC), 1-stearoyl-2-oleoyl-sn-glycero-3-phosphoethanolamine (SOPE), or combinations thereof. In some embodiments, the phosphatidylethanolamine lipid is 1,2-dioleoyl-sn-glycero-3-phosphoethanolamine (DOPE).

In some embodiments, the polyethylene glycol-lipid is selected from 1,2-dimyristoyl-sn-glycerol, methoxypolyethylene glycol (DMG-PEG), DLPE-PEGs, DMPE-PEGs, DPPC-PEGs, and DSPE-PEGs. In some embodiments, wherein the polyethylene glycol-lipid is 1,2-dimyristoyl-sn-glycerol, methoxypolyethylene glycol (DMG-PEG).

In some embodiments, the sterol is selected from cholesterol, campesterol, ergosterol, or sitosterol. In some embodiments, the sterol is selected from cholesterol.

In one embodiment, the agent is a therapeutic agent. In one embodiment, the agent is a diagnostic agent.

The agent delivered into cells can be a polynucleotide. Polynucleotides or oligonucleotides that can be introduced according to the methods herein include DNA, cDNA, and RNA sequences of all types. For example, the polynucleotide can be double stranded DNA, single-stranded DNA, complexed DNA, encapsulated DNA, naked RNA, encapsulated RNA, messenger RNA (mRNA), tRNA, short interfering RNA (siRNA), double stranded RNA (dsRNA), micro-RNA (miRNA), antisense RNA (asRNA) and combinations thereof. The polynucleotides can also be DNA constructs, such as expression vectors, expression vectors encoding a desired gene product (e.g., a gene product homologous or heterologous to the subject into which it is to be introduced), and the like. In one embodiment, the agent is an mRNA.

In one embodiment, the cell is a mammalian cell. In one embodiment, the cell is a human cell. In one embodiment, the cell is a liver cell. In one embodiment, the cell is a blood cell.

In some embodiments, provided herein are methods for delivery of polynucleotides (for example, mRNA) to correct a mutation in a genome. For example, mRNAs can be delivered to correct mutations that cause hemophilia (due to mutations in the genes encoding Factor VIII (F8; hemophilia A) or Factor IX (F9; hemoglobin B).

In one aspect of the disclosure, disclosed herein is a method of treating hemophilia in a subject comprising:
i) administering a composition to the subject, wherein the composition comprises:
a nanoparticle comprising;
  a compound of Formula I, II, III, or IV;
  a non-cationic lipid;
  a polyethylene glycol-lipid;
  a sterol; and
an agent;
and
ii) introducing the agent into the cell of the subject, wherein the agent comprises:

a) a guide RNA that hybridizes with a target sequence of a DNA molecule in a eukaryotic cell that contains the DNA molecule,
b) an mRNA encoding a Cpf1 protein, and
c) an isolated nucleic acid comprising a donor sequence comprising a nucleic acid encoding a truncated FVIII polypeptide;
wherein the cell of the subject contains a genetic mutation in the F8 gene;
wherein the guide RNA hybridizes with the target sequence, wherein the target sequence is in the F8 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA molecule, and
wherein the resultant repaired gene, upon expression, confers improved coagulation functionality to the encoded FVIII protein of the subject compared to the non-repaired F8 gene.

In one aspect of the disclosure, disclosed herein is a method of treating hemophilia in a subject comprising:
i) administering a composition to the subject, wherein the composition comprises:
a nanoparticle comprising;
  a compound of Formula I, II, III, or IV;
  a non-cationic lipid;
  a polyethylene glycol-lipid;
  a sterol; and
an agent;
and
ii) introducing the agent into the cell of the subject, wherein the agent comprises:
a) a guide RNA that hybridizes with a target sequence of a DNA molecule in a eukaryotic cell that contains the DNA molecule,
b) an mRNA encoding a Cpf1 protein, and
c) an isolated nucleic acid comprising a donor sequence comprising a nucleic acid encoding a truncated FIX polypeptide;
wherein the cell of the subject contains a genetic mutation in the F9 gene;
wherein the guide RNA hybridizes with the target sequence, wherein the target sequence is in the F9 gene,
wherein the Cpf1 protein creates a double stranded break in the DNA molecule,
wherein the nucleic acid encoding the truncated FVIII polypeptide is flanked by nucleic acid sequences homologous to the nucleic acid sequences upstream and downstream of the double stranded break in the DNA molecule, and
wherein the resultant repaired gene, upon expression, confers improved coagulation functionality to the encoded FIX protein of the subject compared to the non-repaired F9 gene.

In additional embodiments, the mRNA delivery system and nanoparticles can be used to repair point mutations, truncations, deletions, inversions, or other genetic mutations that are identified as the causal mutation for a genetic disease.

EXAMPLES

The following examples are set forth below to illustrate the compounds, compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. Biodegradable Amino-Ester Nanomaterials for Nucleic Acid Delivery

CRISPR/Cas9 mediated genome editing has been widely used as a powerful tool for biological and therapeutic applications.[1] Adeno-associated virus (AAV) derived vectors and DNA Nanoclews were reported to deliver plasmid-encoding CRISPR/Cas in a wide variety of cells and animal models[2]. Yet, potential off-target effects are significant safety issues if Cas9 is present for long term.[3] One alternative approach is to express Cas9 protein using Cas9 mRNA; however, efficient delivery of Cas9 mRNA is formidable due to its large size (up to 4.5 k nucleotides), high density of negative charges, and weak tolerance of enzymes in serum.[2b] Hence, new biomaterials are needed to overcome this obstacle and enable broad applications of CRISPR/Cas9.

Lipid and lipid-like nanoparticles (LNPs and LLNs) represent one type of biomaterials for efficient delivery of RNAs including siRNA, miRNA, and mRNA.[4] Recently, a few lipid-like nanoparticles based delivery systems demonstrated efficient delivery of mRNAs for expression of functional proteins including factor IX, erythropoietin and Cas9. [4a, 4d, 5] Yet, these lipid-like compounds are not considered to be biodegradable, which may lead to potential side effects. Previous studies reported that biodegradable bonds enabled rapid elimination of lipids from plasma and tissues, and substantially improved their tolerability in preclinical studies.[4f, 6]

Disclosed herein is the design, synthesis and biological evaluation of biodegradable amino-ester derived lipid-like nanoparticles (LLNs) for the delivery of Cas9 mRNA. As shown in scheme 1, four types of lipid chains including ester chain, epoxide chain and acrylate chain (termed as A, Ab, E, and O) on four amino cores (termed as DMPA, MPA, PA, and AEPA) were synthesized. E and O series were reported previously for siRNA delivery[4c, 4f], serving as control groups. MPA-A did show fast hydrolysis in the presence of esterases from porcine liver. Moreover, the rate of biodegradability can be tuned by chemical modification of the lipid chain. For example, clearance rate of MPA-Ab is significantly slowed down compared to MPA-A. Most importantly, both MPA-A and MPA-Ab demonstrate efficient delivery of Cas9 mRNA in cell and animal models.

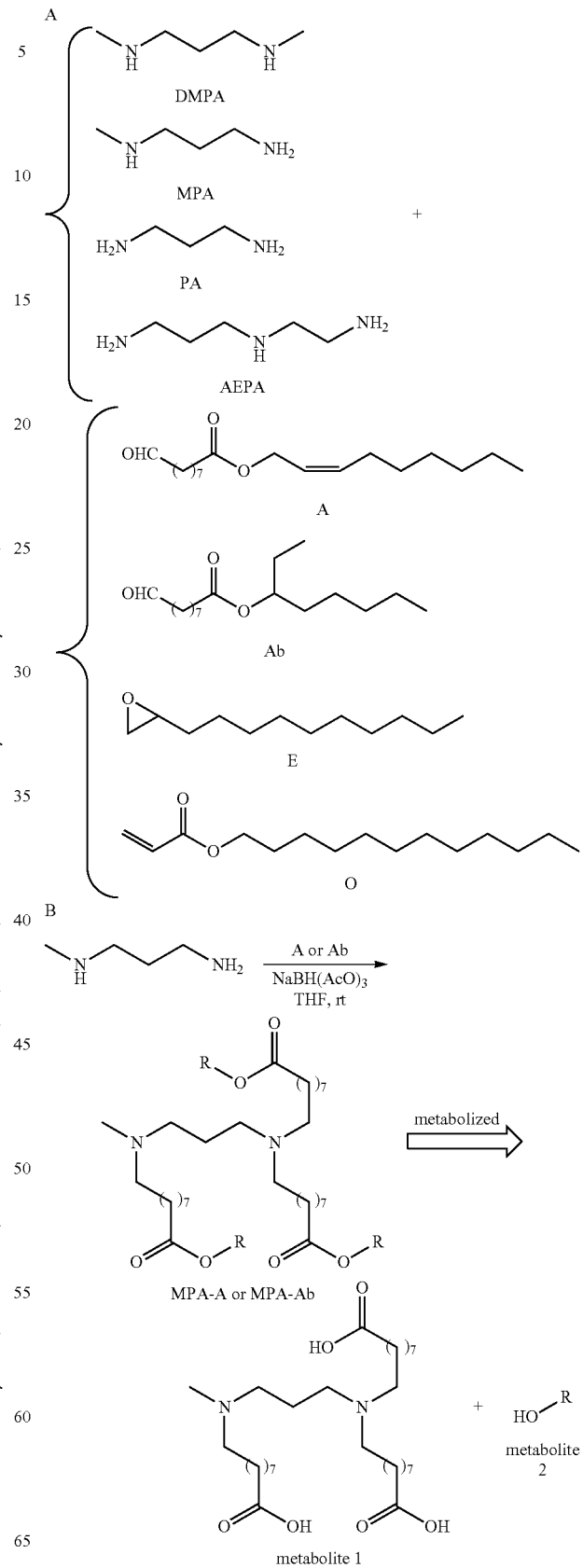

-continued

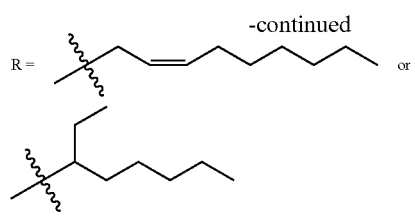

(A) Synthesis of amino-ester derived lipid-like compounds. (B) Rationale of biodegradability for newly synthesized lipid-like compounds. It is likely that MPA-A and MPA-Ab will be degraded to metabolites 1 and 2 by esterase.

Figure 1B:
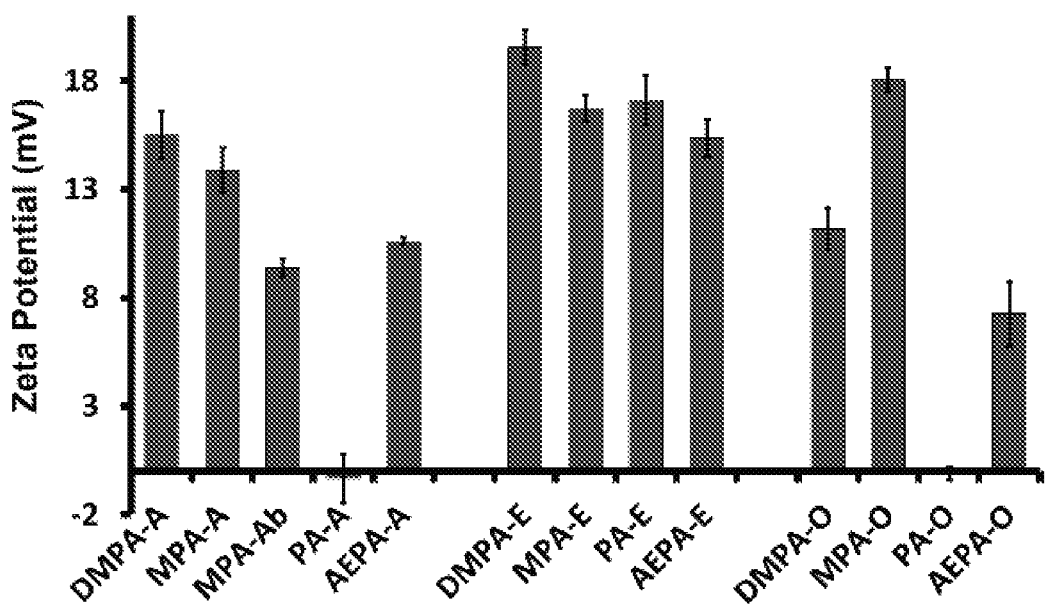
Figure 1C:
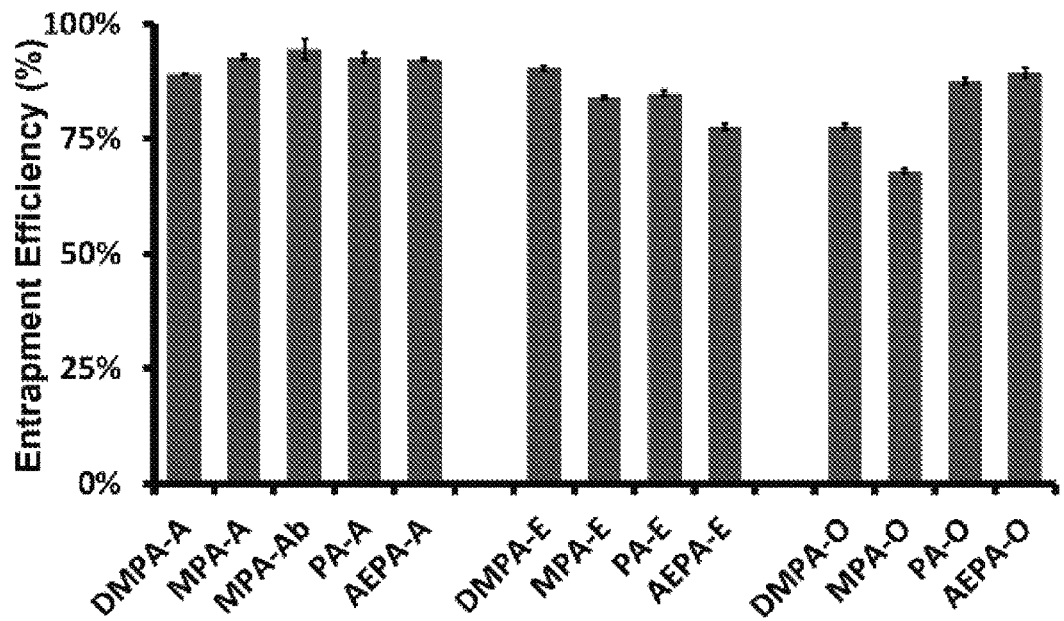

First, lipid chains A and Ab were installed on the four amines through a reductive amination reaction to afford amino-ester derived lipid-like compounds (scheme 1A). Epoxide (E) and acrylate (O) series were synthesized according to the procedures reported previously.[4c, 4f] Structures of the products were validated by $^1$HNMR and mass spectrometry (Supporting information). According to the methods reported previously[4, 7], newly synthesized amino-ester derived lipid-like compounds were formulated with 2-dioleoyl-sn-glycero-3-phosphoethanolamine (DOPE), cholesterol (Chol), 1,2-dimyristoyl-sn-glycerol, methoxypolyethylene glycol (DMG-PEG$_{2000}$) as well as Cas9 mRNA. Particle properties including particle size, zeta potential and entrapment efficiency of Cas9 mRNA were measured using a Zetasizer Nano ZS and a ribogreen assay, respectively (FIG. 1A-C). Size of these particles ranged from 119 to 184 nm with PDI<0.3. The entrapment efficiency of mRNA was up to 94%.

Figure 1D:
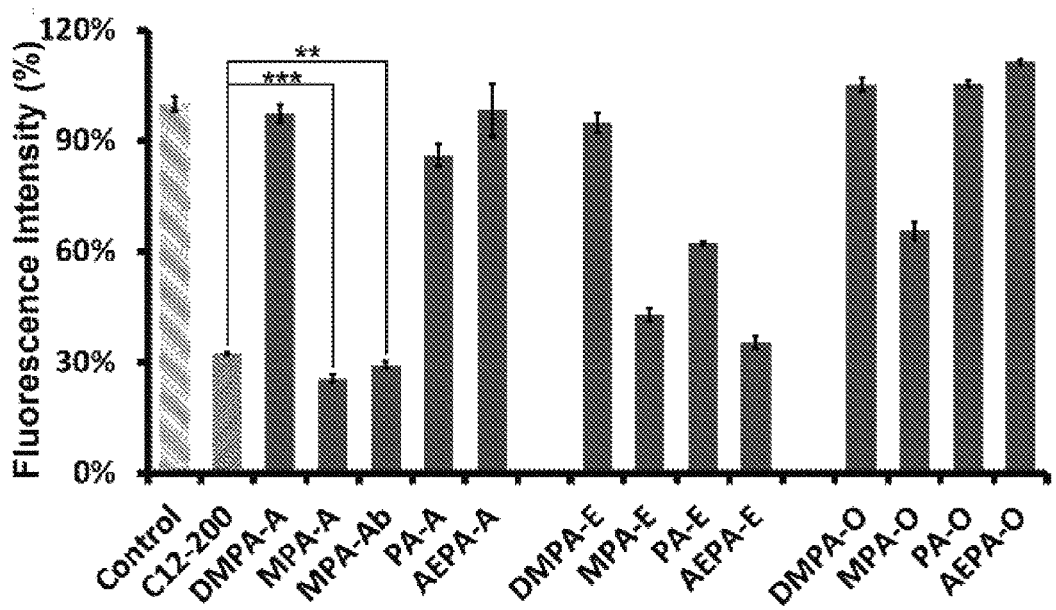

Then, delivery efficiency of Cas9 mRNA was evaluated in HEK293T cells that stably express eGFP and the corresponding eGFP guide RNA (Efficient delivery of Cas9 mRNA induces reduction of eGFP signals in these cells). HEK293T cells were treated with newly formulated LLNs at a Cas9 mRNA dose of 50 ng per well in a 24-well clear bottom plate. 48 hrs after treatment, eGFP signal was quantified using fluorescence-activated cell sorting (FACS) analysis. Six types of LLNs displayed dramatic reduction of eGFP signal (FIG. 1D). Importantly, MPA-A and MPA-Ab decreased eGFP signal 74% and 70%, respectively, which showed significantly higher delivery efficiency compared to other LLNs including C12-200, a lead material reported previously (see structure below for comparison; Love, Kevin, T. et. al. Proc. Natl. Acad. Sci. U.S.A. 2010, 107, 1864-1869).[2e] Based on the in vitro results, MPA-A and MPA-Ab were selected for further studies.

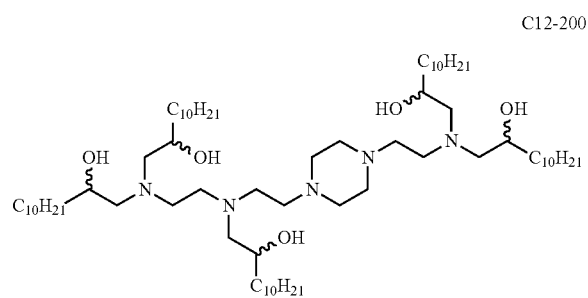

Next, biodegradability of MPA-A and MPA-Ab using MPA-E as a control group was investigated. The degradation assay was carried out under 37° C. using esterase according to the method reported in the literature.[8] Amount of the compounds were quantified through a mass spectra analysis.

Figure 2A:
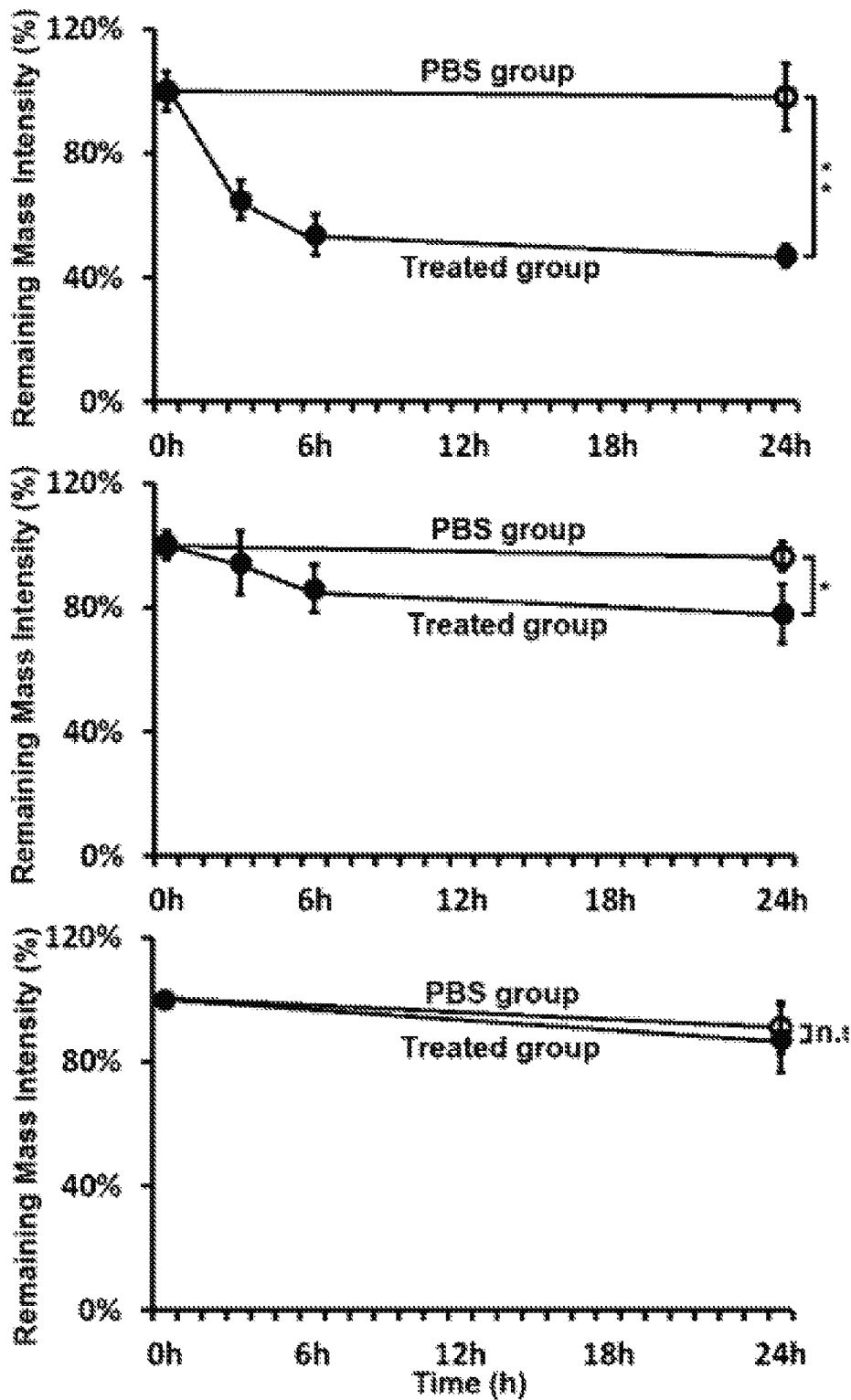
FIGS. 2A-2B. Degradation of amino-ester lipid-like nanpparticles (LLNs).
Figure 2B:
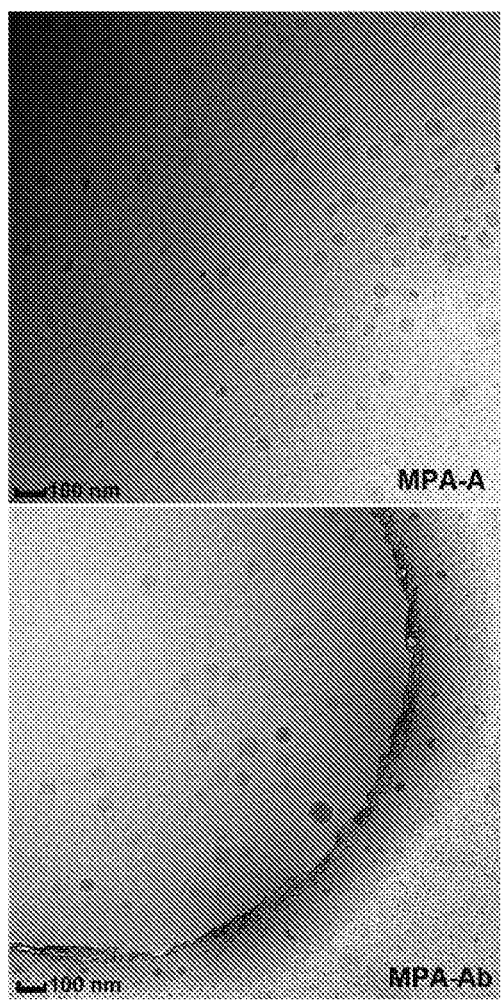

As shown in FIG. 2A, over 53% of MPA-A was degraded 24 h after incubation, respectively, while 22% of MPA-Ab was degraded at the same condition after 24 h incubation. In addition, MPA-E, a non-biodegradable control, showed no significant change of mass spectra intensity after 24 h treatment with esterase. These results demonstrated our design, that is, branched lipid chains are capable of slowing down the degradation rate due to the heavy steric effects. Cryo-TEM images revealed that both MPA-A and MPA-Ab LLNs were spherical with relatively homogenous particle size (FIG. 2B).

Figure 3:
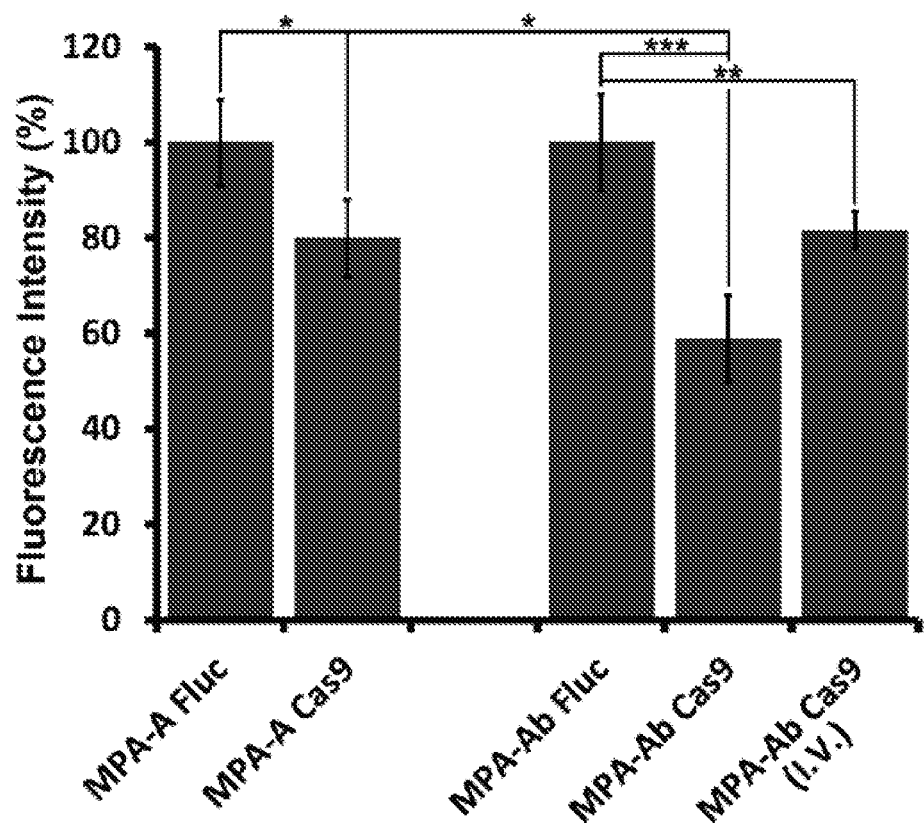
FIG. 3. In vivo delivery of Cas9 mRNA. Both MPA-A and MPA-Ab LLNs encapsulating Cas9 mRNA significantly reduced eGFP signal in a mouse xenograft model. (n=4; *, P<0.05; , P<0.01; *, P<0.001; t test, double-tailed).

Given the promising in vitro results, MPA-A and MPA-Ab LLNs were then examined for their delivery efficiency of Cas9 mRNA in vivo. A mouse xenograft tumor model was established using the HEK293T cells mentioned above. Mice bearing xenograft tumors were randomly divided into five groups (n=4), and injected intratumorally for four groups with treated groups (MPA-A/Cas9 LLNs and MPA-Ab/Cas9 LLNs) and control groups (MPA-A/Fluc (Firefly Luciferase) LLNs and MPA-Ab/Fluc LLNs) at a dose 2.5 µg/100 mm³ tumor; for the last group, MPA-Ab/Cas9 LLNs was injected intravenously at a dose 0.88 mg/kg. Five days after treatment, tumors were dissected and lysed. Similarly, eGFP signal was quantified using fluorescence-activated cell sorting (FACS) analysis. As shown in FIG. 3, both MPA-A LLNs and MPA-Ab LLNs showed significant suppression of eGFP signal compared to the control groups, demonstrating efficient delivery of Cas9 mRNA in vivo. More importantly, MPA-Ab LLNs (41% reduction) was more potent than MPA-A LLNs (20% reduction) when injected intratumorally. Amazingly, MPA-Ab LLNs also showed significant reduction of eGFP signal (18%) when injected intravenously.

In summary, a series of biodegradable amino-ester lipid-like nanoparticles for nucleic acid delivery (for example, Cas9 mRNA) were designed. By modulating functional groups on the lipid chains, the rate of their biodegradability could be unexpectedly enhanced. For example, MPA-A degraded over 53% at after 24 h incubation with esterases from porcine liver, while MPA-Ab degraded around 22% in the same condition. In addition both MPA-A and MPA-Ab showed higher delivery efficiency for Cas9 mRNA compared to E & O series LLNs and C12-200 a lead material reported previously. Moreover, both MPA-A and MPA-Ab LLNs exhibits significant delivery of Cas9 mRNA in vivo.

Methods

Synthesis of Nanomaterials:

ester chains A and Ab were synthesized according to methods reported previously.[9]

General method for the synthesis of DMPA-A, MPA-A, MPA-Ab, PA-A, AEPA-A. Excess amount of A or Ab and 0.1 mmol corresponding amine were stirred in 5 mL anhydrous tetrahydrofuran at RT. After adding NaBH(OAc)$_3$, reaction mixture was stirred at RT for 12 h. After the solvent was evaporated, the residue was purified by column chromatography using a Combiflash Rf system with gradient elution from 100% CH$_2$Cl$_2$ to CH$_2$Cl$_2$/MeOH/NH$_4$OH (75/22/3 by volume) to give the products.

Method for the Biodegradation Assay:

MPA-A, MPA-Ab and MPA-E were dissolved with acetone to obtain 3.24 mol/L stock solutions. In a typical assay, 15 µL of stock solution was added into 485 µL of PBS with or without esterase (0.8 mg/mL) and bile salt (5 mg/mL) in a 1.5 mL sealed tube and shake at 37° C. for fixed time as 0 h, 3 h, 6 h, and 24 h. The degradation was stopped by adding 1 mL of dichloromethane. The organic phase was used for mass spectrometry analysis (Bruker amaZon ETD).

The degradation percentage was calculated by the intensity of molecular ion peak using Compass OpenAccess mass spectrometry software.

Formulation of mRNA-Loaded LLNs:

LLNs were formulated with 2-dioleoyl-sn-glycero-3-phosphoethanolamine (DOPE), cholesterol, 1,2-dimyristoyl-snglycerol, methoxypolyethylene glycol (DMG-PEG$_{2000}$) (molar ratio 20/30/40/0.75), and Cas9 mRNA or Fluc mRNA via pipetting for in vitro studies or via a microfluidic based mixing device (Precision NanoSystems) for in vivo studies. For in vivo studies, the freshly prepared LLNs were dialyzed in PBS buffer using Slide-A-Lyzer dialysis cassettes (3.5 K MWCO, Life Technologies, Grand Island, N.Y.). Particle size and zeta potential of LLNs were measured using a NanoZS Zetasizer (Malvern, Worcestershire, U.K.) at a scattering angle of 173° and a temperature of 25° C. Entrapment efficiency of LLNs was determined using the Ribogreen assay reported previously.[4c, 10]

Cryo-Transmission Electron Microscopy (Cryo-TEM):

Cryo-TEM specimens were prepared by thin-film plunge-freezing[11]. A small aliquot (2.5 μL) of MPA-A or MPA-Ab LLNs was applied to a C-flat TEM grid (EMS, Hatfield, Pa.) inside a FEI Mark IV Vitrobot (FEI, Hillsboro, Oreg.). After the blotting process using filter papers, the grid was immediately plunged into liquid ethane to achieve vitrified electron-transparent thin films. The grid was transferred under liquid nitrogen in cryo-transfer station to a Gatan 626.DH cryo-TEM holder (Gatan, Pleasanton, Calif.). The cryo-TEM holder was loaded to a Tecnai F20 S/TEM (FEI, Hillsboro, Oreg.) and the specimen temperature was maintained at <170° C. Cryo-TEM images were recorded using a Gatan Ultrascan 4K CCD camera under low dose conditions.

In Vitro Delivery of Cas9 mRNA:

293T cells that stably expressing eGFP and corresponding gRNA were seeded in one 24-well clear bottom plate (2×10$^4$ cells/500 μl). After 24 h incubation, 5 μL LLNs containing Cas9 mRNA were added with PBS as a control group. 5 μL of PBS was added to control group. 48 h after treatment, cells were collected and the eGFP signal was quantified with BD LSR II flow cytometry analyzer (BD Biosciences, San Jose, Calif.).

In Vivo Studies of MPA-A and MPA-Ab LLNs for Cas9 mRNA Delivery:

All procedures used in animal studies were approved by the Institutional Animal Care and Use Committee (IACUC) at The Ohio State University and were also consistent with local, state, and federal regulations as applicable. NU/J, Homozygous female mice (9 weeks old) were purchased from The Jackson Laboratory. To establish xenograft model, 100 μL of HEK293T cells (3×10$^7$/mL) that stably express eGFP and corresponding gRNA were suspended in PBS and subcutaneously injected into the right flank of the mice. Mice was euthanized and subcutaneous tumors were harvested when the subcutaneous nodule reaches to about 800 mm$^3$ in size. The tumor-like bulge was carefully isolated to remove any fat and necrotic tissue, and cut into small pieces (approximately 2 mm$^3$ in diameter) under aseptic conditions. Each individual piece was inserted into the right incision of each receptor mouse made by surgical scissors using forceps. The incision site was immediately closed with one drop of 3M Vetbond tissue adhesive. Three weeks later, the mice inoculated with tumor-like piece were randomly divided into five groups (n=4), and injected intratumorally for four groups with lipid particles WA-A/Cas9 and WA-A/Fluc (control) or MPA-Ab/Cas9 and MPA-A/Fluc (control) (0.05 mg/mL, 50 uL/100 mm$^3$); for the last group, MPA-Ab/Cas9 LLNs was injected intravenously at a dose 0.88 mg/kg. Five days after treatment, tumor-like bulges were isolated and dissociated with Tumor Dissociation Kit_human (Miltenyi Biotec). The eGFP signal was measured with a BD LSR II flow cytometry analyzer (BD Biosciences, San Jose, Calif.)

REFERENCES CITED IN THIS EXAMPLE

[1] a) L. Cong, F. A. Ran, D. Cox, S. Lin, R. Barretto, N. Habib, P. D. Hsu, X. Wu, W. Jiang, L. A. Marraffini, F. Zhang, Science, 2013, 339, 819; b) M. Prashant, Y. Luhan, M. E. Kevin, A. John, G. Marc, E. D. James, E. N. Julie, M. C. George, Science, 2013, 339, 823; c) P. D. Hsu, D. A. Scott, J. A. Weinstein, F. A. Ran, S. Konermann, V. Agarwala, Y. Li, E. J. Fine, X. Wu, O. Shalem, T. J. Cradick, L. A. Marraffini, G. Bao, F. Zhang, Nat. Biotechnol. 2013, 31, 827; d) N. Chang, C. Sun, L. Gao, D. Zhu, X. Xu, X. Zhu, J. Xiong, J. Xi, Cell Res. 2013, 23, 465; e) M. Jinek, K. Chylinski, I. Fonfara, M. Hauer, Jennifer A. Doudna, E. Charpentie, Science, 2012, 337, 816.

[2] a) A. E. Friedland, R. Baral, P. Singhal, K. Loveluck, S. Shen, M. Sanchez, E. Marco, G. M. Gotta, M. L. Maeder, E. M. Kennedy, A. V. R. Kornepati, A. Sousa, M. A. Collins, H. Jayaram, B. R. Cullen, D. Bumcrot, Genome Biol. 2015, 16, 257; b) F. Ran, L. Cong, W. Yan, D. Scott, J. Gootenberg, A. Kriz, B. Zetsche, O. Shalem, X. Wu, K. Makarova, E. Koonin, P. Sharp, F. Zhang, Nature, 2015, 520, 186; c) R. J. Platt, S. Chen, Y. Zhou, M. J. Yim, L. Swiech, H. R. Kempton, J. E. Dahlman, O. Parnas, T. M. Eisenhaure, M. Jovanovic, D. B. Graham, S. Jhunjhunwala, M. Heidenreich, R. J. Xavier, R. Langer, D. G. Anderson, N. Hacohen, A. Regev, G. Feng, P. A. Sharp, F. Zhang, Cell, 2014, 159, 440; d) W. Sun, W. Ji, J. M. Hall, Q. Hu, C. Wang, C. L. Beisel, Z. Gu, Angew. Chem. Int. Ed. 2015, 54, 12029; e) H. Yin, C. Song, J. R. Dorkin, L. J. Zhu, Y. Li, Q. Wu, A. Park, J. Yang, S. Suresh, A. Bizhanova, A. Gupta, M. F. Bolukbasi, S. Walsh, R. L. Bogorad, G. Gao, Z. Weng, Y. Dong, V. Koteliansky, S. A. Wolfe, R. Langer, W. Xue, D. G. Anderson, Nat. Biotechnol. 2016, 33, 139.

[3] Y. Fu, J. A. Foden, C. Khayter, M. L. Maeder, D. Reyon, J. K. Joung, J. D. Sander, Nat. Biotechnol. 2013, 31, 822.

[4] a) B. Li, X. Luo, B. Deng, J. Wang, D. W. McComb, Y. Shi, K. M. L. Gaensler, X. Tan, A. L. Dunn, B. A. Kerlin, Y. Dong, Nano Lett. 2015, 15, 8099; b) Y. Dong, K. T. Love, J. R. Dorkin, S. Sirirungruang, Y. Zhang, D. Chen, R. L. Bogorad, H. Yin, Y. Chen, A. J. Vegas, C. A. Alabi, G. Sahay, K. T. Olejnik, W. Wang, A. Schroeder, A. K. Lytton-Jean, D. J. Siegwart, A. Akinc, C. Barnes, S. A. Barros, M. Carioto, K. Fitzgerald, J. Hettinger, V. Kumar, T. I. Novobrantseva, J. Qin, W. Querbes, V. Koteliansky, R. Langer, D. G. Anderson, Proc. Natl. Acad. Sci. U.S.A. 2014, 111, 3955; c) K. T. Love, K. P. Mahon, C. G. Levins, K. A. Whitehead, W. Querbes, J. R. Dorkin, J. Qin, W. Cantley, L. L. Qin, T. Racie, M. Frank-Kamenetsky, K. N. Yip, R. Alvarez, D. W. Y. Sah, A. de Fougerolles, K. Fitzgerald, V. Koteliansky, A. Akinc, R. Langer, D. G. Anderson, Proc. Natl. Acad. Sci. U.S.A. 2010, 107, 1864; d) O. S. Fenton, K. J. Kauffman, R. L. McClellan, E. A. Appel, J. R. Dorkin, M. W. Tibbitt, M. W. Heartlein, F. DeRosa, R. Langer, D. G. Anderson, Adv. Mater. 2016, 28, 2939; e) R. Kanasty, J. R. Dorkin, A. Vegas, D. Anderson, Nat. Mater. 2013, 12, 967; f) K. A. Whitehead, J. R. Dorkin, A. J. Vegas, P. H. Chang, O. Veiseh, J. Matthews, O. S. Fenton, Y. Zhang, K. T.

Olejnik, V. Yesilyurt, D. Chen, S. Barros, B. Klebanov, T. Novobrantseva, R. Langer, D. G. Anderson, *Nat. Commun.* 2014, 5, 4277.

[5] a) K. Kariko, H. Muramatsu, J. M. Keller, D. Weissman, *Mol. Ther.* 2012, 20, 948; b) Y. Dong, J. R. Dorkin, W. Wang, P. H. Chang, M. J. Webber, B. C. Tang, J. Yang, I. Abutbul-Ionita, D. Danino, F. DeRosa, M. Heartlein, R. Langer, D. G. Anderson, *Nano Lett.* 2016, 16, 842; c) K. J. Kauffman, J. R. Dorkin, J. H. Yang, M. W. Heartlein, F. DeRosa, F. F. Mir, O. S. Fenton, D. G. Anderson, *Nano Lett.* 2015, 15,7300.

[6] M. A. Maier, M. Jayaraman, S. Matsuda, J. Liu, S.t Barros, W. Querbes, Y. K Tam, S. M. Ansell, V. Kumar. J. Qin. X. Zhang, Q. Wang, S. Panesar, R. Hutabarat, M. Carioto, J. Hettinger, P. Kandasamy, D. Butler, K. G. Rajeev, B. Pang, K. Charisse, K. Fitzgerald, B. L Mui, X. Du, P. Cullis, T. D. Madden, M. J. Hope, M. Manoharan, A. Akinc, *Mol. Ther.* 2013, 21, 1570.

[7] Y. Dong, A. A. Eltoukhy, C. A. Alabi, O. F. Khan, O. Veiseh, J. R. Dorkin, S. Sirirungruang, H. Yin, B. C. Tang, J. M. Pelet, D. Chen, Z. Gu, Y. Xue, R. Langer, D. G. Anderson, *Adv. Healthcare Mater,* 2014, 3, 1392.

[8] H. Oda, H. Yamashita, K. Kosahara, S. Kuroki, F. Nakayama, *J. Lipid Res.* 1990, 31, 2209.

[9] a) M. Rajabi, M. Lanfranchi, F. Campo, L. Panza, *Synth. Commun.* 2014, 44, 1149; b) S. R. Woodcock, A. J. V. Marwitz, P. Bruno, B. P. Branchaud, *Org. Lett.* 2006, 8, 3931.

[10] D. Chen, K. T. Love, Y. Chen, A. A. Eltoukhy, C. Kastrup, G. Sahay, A. Jeon, Y. Dong, K. A. Whitehead, D. G. Anderson, *J. Am. Chem. Soc.* 2012, 134, 6948.

[11] M. Gao, Y. K. Kim, C. Zhang, V. Borshch, S. Zhou, H. S. Park, A. Jákli, O. D. Lavrentovich, M. G. Tamba, A. Kohlmeier, G. H. Mehl, W. Weissflog, D. Studer, B. Zuber, H. Gnägi, F. Lin, *Microsc. Res. Tech.* 2014, 77, 754.

Materials.

ψ-modified Cas9 mRNA and 5meC-ψ-modified Firefly Luciferase mRNA were purchased from TriLink Biotechnologies, Inc. (San Diego, Calif.). 1,2-dioleoyl-sn-glycero-3-phosphoethanolamine (DOPE) was purchased from Avanti Polar Lipids, Inc. Other chemicals were purchased from sigma-Aldrich and used without further purification.

Synthesis.

9-oxononanoic acid, ester chain A and Ab were synthesized according to reported method.[s1]

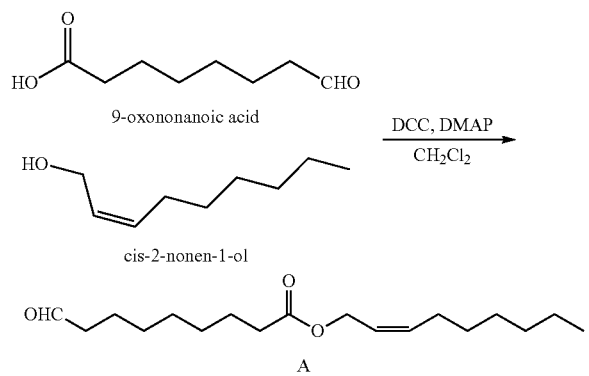

A

A: 9-oxononanoic acid (500 mg, 3.16 mmol) and DCC (700 mg, 3.40 mmol) were dissolved in 15 mL $CH_2Cl_2$ and cooled to 0° C. After adding DMAP (10 mg, 0.08 mmol), the reaction mixture was stirred for 30 min at 0° C. Cis-2-nonen-1-ol (670 mg, 4.72 mmol) was added and stirred for 2 h at 0° C. The reaction mixture was warmed to RT and stirred overnight. The reacting mixture was then washed with water twice. The organic phase was dried with sodium sulfate and $CH_2Cl_2$ was evaporated. The crude product was purified by column chromatography using a Combiflash Rf system with elution hexanes/ethyl acetate, (95/5 by volume) to give the product colorless oil 650 mg, yield 69.4%.

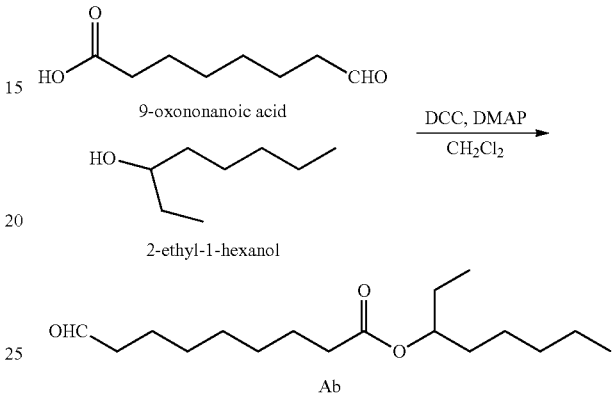

Ab

Ab: Following the same procedure as described above for A.

MPA-A: yield 42.2%, $^1$H NMR (400 MHz, $CDCl_3$) δ=5.65 (3H, m), 5.56 (3H, m), 4.65-4.63 (6H, d, J=8), 2.44 (6H, m), 2.34-2.30 (8H, t, J=8), 2.24 (3H, s), 2.14-2.09 (6H, m), 1.65-1.62 (9H, m), 1.46 (6H, m), 1.40-1.30 (50H, m), 0.92-0.88 (9H, t, J=8). MS (m/z): $[M+H]^+$ calcd. for $C_{58}H_{109}N_2O_6$, 929.8286; found, 929.8266.

DMPA-A: yield 77.0%, $^1$H NMR (400 MHz, $CDCl_3$) δ=5.65 (2H, m), 5.55 (2H, m), 4.65-4.63 (4H, d, J=8), 2.42-2.39 (8H, m), 2.37-2.32 (4H, t, J=8), 2.26 (6H, s), 2.14-2.09 (4H, m), 1.73-1.62 (6H, m), 1.49 (4H, m), 1.40-1.31 (32H, m), 0.92-0.89 (6H, t, J=8). MS (m/z): $[M+H]^+$ calcd. for $C_{41}H_{79}N_2O_4$, 663.6040; found, 663.6014.

PA-A: yield 61.9%, $^1$H NMR (400 MHz, $CDCl_3$) δ=5.64 (4H, m), 5.55 (4H, m), 4.64-4.63 (8H, d, J=8), 2.42 (10H, m), 2.34-2.30 (8H, t, J=8), 2.14-2.09 (8H, m), 1.65-1.62 (10H, m), 1.44-1.30 (74H, m), 0.92-0.88 (12H, t, J=8). MS (m/z): $[M+H]^+$ calcd. for $C_{75}H_{139}N_2O_8$, 1196.0531; found, 1196.0490.

AEPA-A: yield 69.4%, $^1$H NMR (400 MHz, $CDCl_3$) δ=5.64 (5H, m), 5.55 (5H, m), 4.65-4.63 (10H, d, J=8), 2.53 (5H, s), 2.43 (11H, s), 2.34-2.30 (10H, t, J=8), 2.14-2.09 (10H, m), 1.66-1.62 (12H, m), 1.44-1.31 (92H, m), 0.92-0.88 (15H, t, J=8). MS (m/z): $[M+H]^+$ calcd. for $C_{95}H_{176}N_3O_{10}$, 1519.3356; found, 1519.3313.

DMP-A: yield 74.0%, $^1$H NMR (400 MHz, $CDCl_3$) δ=4.85-4.80 (3H, m), 2.47 (6H, m), 2.46-2.28 (10H, m), 2.25 (3H, s), 1.65-1.45 (26H, m), 1.31 (42H, m), 0.91-0.87 (18H, m). MS (m/z): $[M+H]^+$ calcd. for $C_{55}H_{109}N_2O_6$, 893.8286; found, 893.8275.

Example 2. Characterization of Amino-Ester Nanomaterials

Figure 4A:
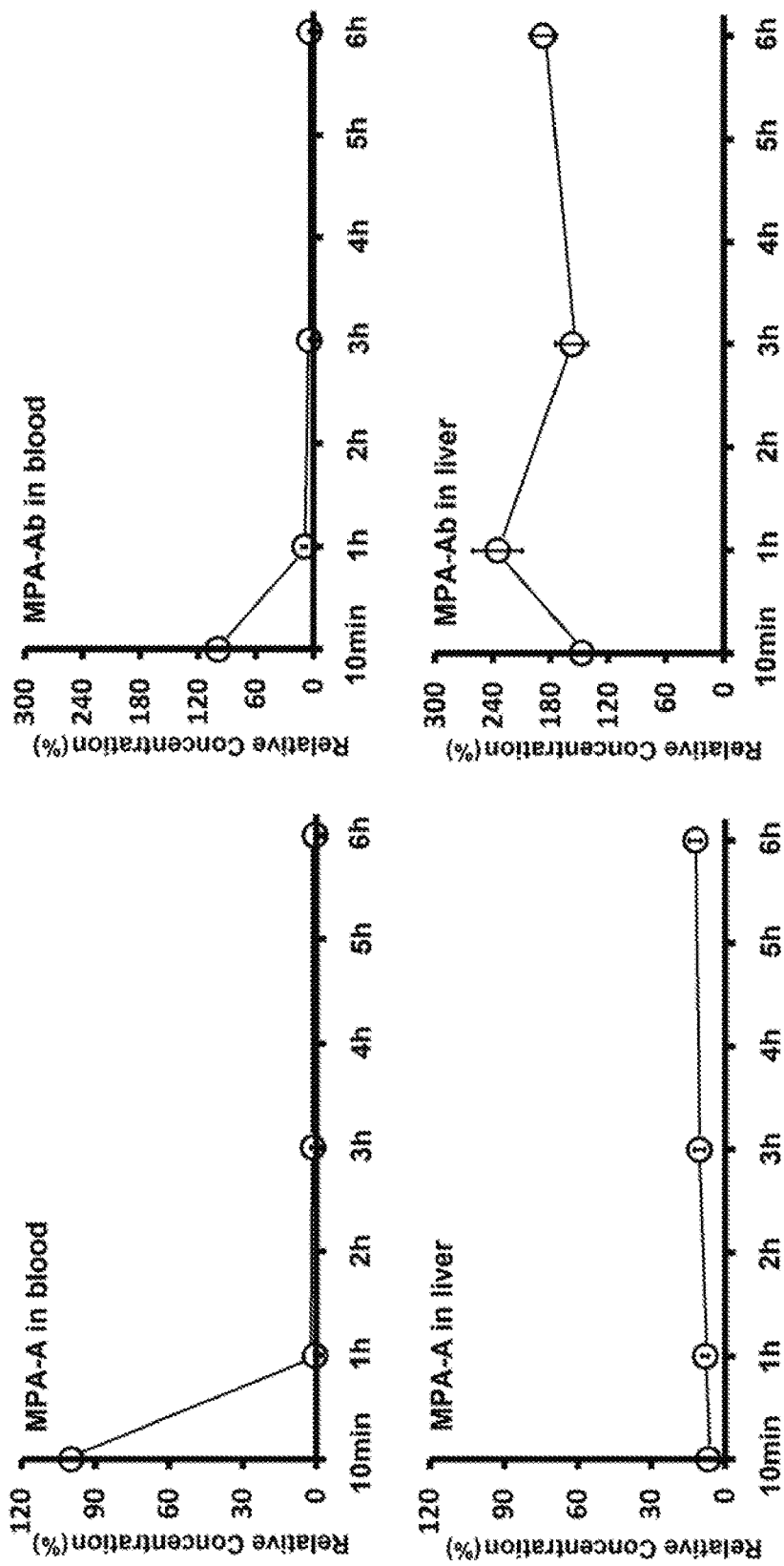
FIGS. 4A-4B. Analysis of MPA-A and MPA-Ab.

Next, the pharmacokinetics and the histopathology of amino ester LLNs in mice were analyzed. As shown in FIG. 4A, MAP-A and MPA-Ab showed decreased concentrations in the blood within one hour.

Figure 4B:
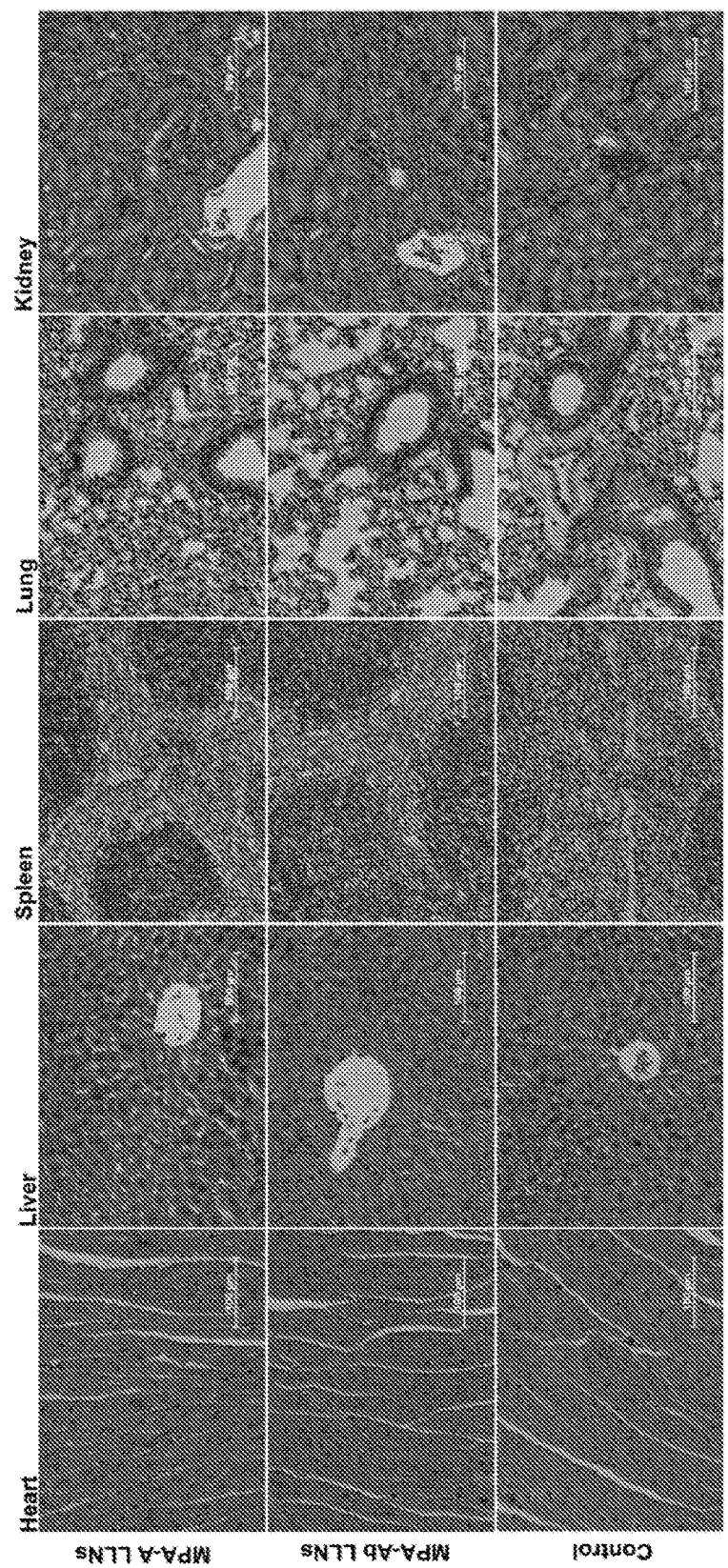

In addition to delivery efficiency, the clinical use of gene-editing tools requires an acceptable safety profile. A single-dose toxicity study of lipid nanoparticles is conducted, followed by histopathology in mice dosed at 0.5 mg/kg. Samples were collected and no histological abnormalities were observed in the liver, spleen, kidney, heart, or lung (FIG. 4B). This single-dose toxicity study shows that lipid nanoparticles can be well tolerated in mice at this dose.

Figure 5:
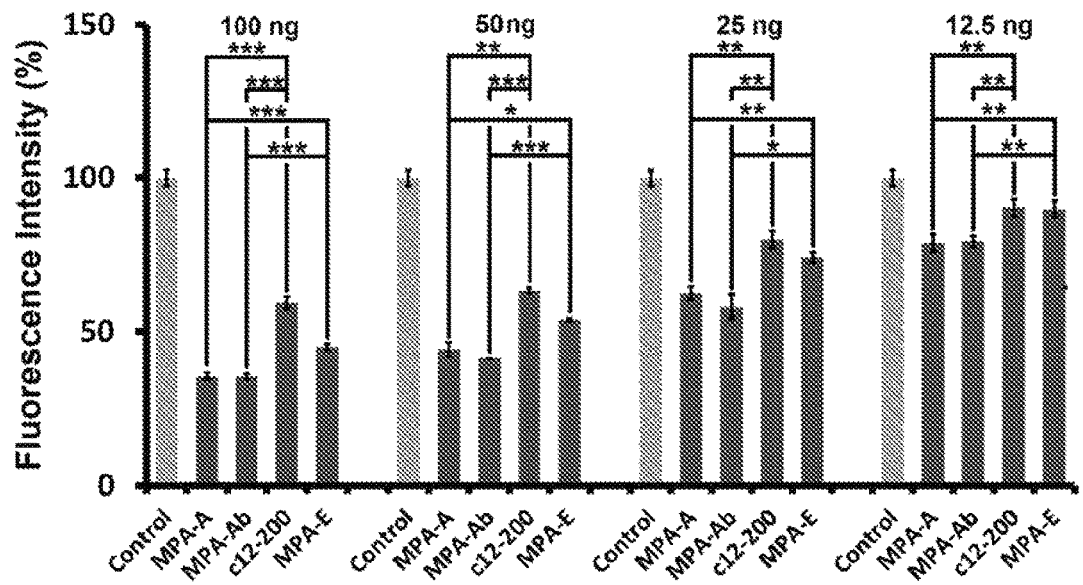

Next, the dose dependency of amino ester compounds on delivery efficiency of Cas9 mRNA was evaluated in HEK293T cells that stably express eGFP and the corresponding eGFP guide RNA (Efficient delivery of Cas9 mRNA induces reduction of eGFP signals in these cells). HEK293T cells were treated with newly formulated LLNs at a Cas9 mRNA dose of 50 ng per well in a 24-well clear bottom plate. 48 hrs after treatment, eGFP signal was quantified using fluorescence-activated cell sorting (FACS) analysis. As shown in FIG. 5, MPA-A and MPA-Ab showed higher delivery efficiency compared to other LLNs including C12-200, a lead material reported previously.[2e]

Figure 6:
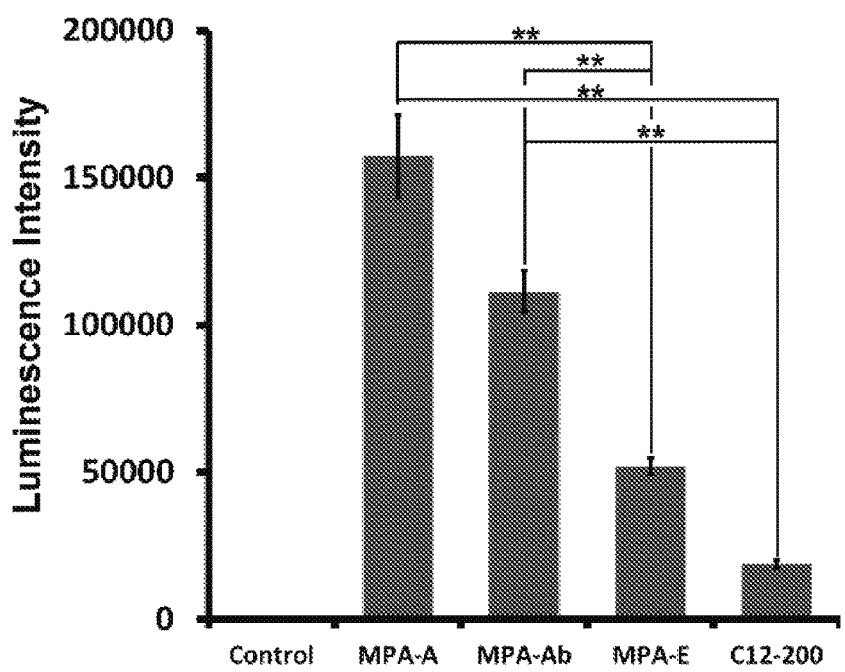
FIG. 6. Delivery of mRNA encoding firefly luciferase in Hep3B cells. Control: PBS. (triplicate; **, P<0.01; t test, double-tailed).

An in vitro delivery model using Hep3B cells, a human hepatoma cell line, was analyzed. Hep3B cells were seeded (20,000 cells/well) into each well of an opaque white 96-well plate and allowed to attach overnight in growth medium. Growth medium was composed of 90% phenol red-free EMEM and 10% FBS. Lipid nanoparticles were formulated with luciferase mRNA. Cells were transfected by addition of formulated lipid mRNA nanoparticles to growth medium. Transfections were performed in triplicate. 6 h after transfection, cells were analyzed for luciferase expression with LS 55 Fluorescence Spectrometer. MPA-A and MPA-Ab showed significant luciferase expression compared to MPA-E, C12-200 or control (PBS)(FIG. 6).

In addition to luciferase, LLNs were tested for delivery of eGFP. As shown in FIG. 7, most cells showed some eGFP expression. However, MPA-A and MPA-Ab shows higher levels of eGFP expression compared to MPA-E, C12-200 or control (PBS)(FIG. 7).

Figure 9:
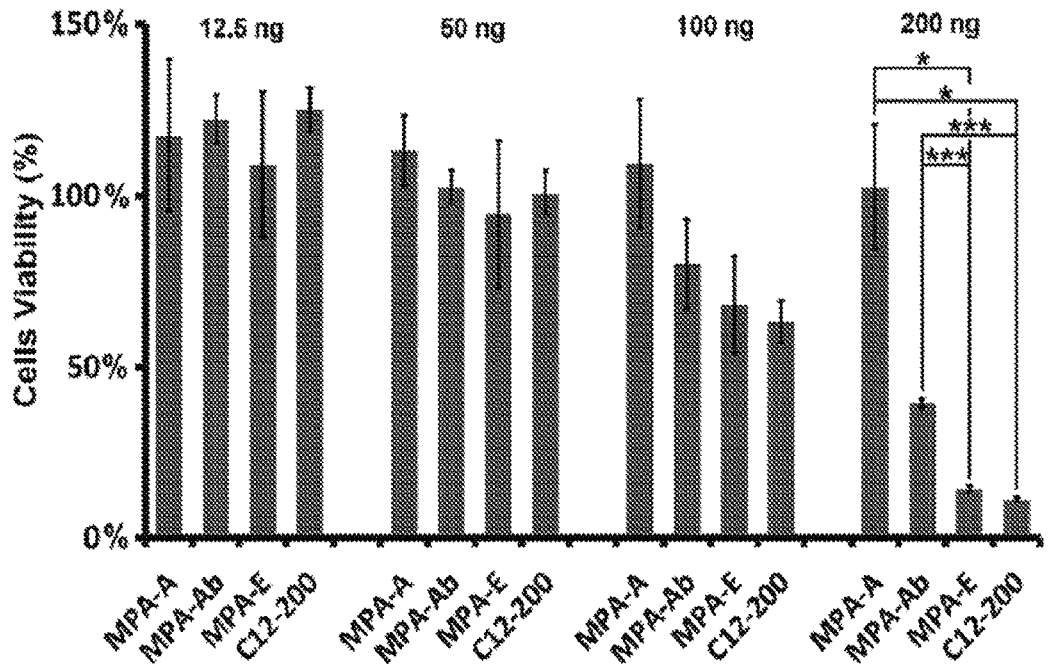
FIG. 9. Cell viability as measured in the MTT assay on Hep3B cell line at mRNA dose of 12.5, 50 100 and 200 ng. (triplicate; *, P<0.05; , P<0.01; *, P<0.001; t test, double-tailed).

Amino ester LLNs were also analyzed for effects on cell viability. 293T cells or Hep3B cells were grown in 96-well plates in 150 μL of medium 24 h prior to treatment at a density of $2 \times 10^4$ cells/well. After 6 h incubation with free FLuc mRNA or LLNs, 17 μL of MTT (5 mg/mL solution in PBS) was added to each well and the cells were then incubated for 4 h at 37° C. Then the medium was removed, and 150 μL of dimethyl sulfoxide was added. After shaking for 10 min, the absorbance at a wavelength of 570 nm was measured on a SpectraMax M5 microplate reader. Cell viability of amino ester LLNs was normalized by untreated cells. 3-(4,5-dimethylthiazol-2-yl)-2,5-diphenyltetrazolium bromide (MTT) was purchased from Amresco (Solon, Ohio). As shown in FIGS. 8 and 9, cell viability was higher in 293T or Hep3B cells for both MPA-A and MPA-Ab when compared to treatment with MPA-E or C12-200.

Example 3. Use of Amino Ester Lipid-Like Nanoparticles (LLNs) in a Gene-Editing System for Hemophilia B Hemophilia is an inherited genetic disorder with an incidence of 1:5000 live born males (Coppola A, et al. Journal of blood medicine. 2010; 1:183-95; Monahan P E, et al. Current opinion in hematology. 2002; 9(5): 430-6; Sabatino D E, et al. Animal models of hemophilia. Progress in molecular biology and translational science. 2012; 105: 151-209). The disorder affects an estimated 20,000 patients in the US and over 400,000 patients worldwide, one quarter of which is affiliated with hemophilia B (HB) due to FIX mutations. Patients with hemophilia suffer life-threatening bleeding complications and debilitating joint diseases. Based on the level of clotting factor activity, HB is usually classified into three groups: mild hemophilia B (6% up to 40% of FIX in the blood); moderate hemophilia B (1% to 5% of FIX in the blood); severe hemophilia B (<1%). Current therapy is to infuse FIX protein concentrates in order to treat or to prevent bleeding. Yet, approximately 75% of patients with hemophilia have limited or no access to treatment. Moreover, therapeutic efficacy has always been hampered by the development of antibodies against FIX in 30% of patients with severe HB. Therefore, new treatment strategies are in urgent demand in order to improve therapeutic benefits and patient compliance.

Genome engineering holds enormous potential for treating a wide variety of genetic disorders (Kim H, Kim J S. Nat Rev Genet. 2014; 15(5):321-34; Damian M, Porteus M H. Mol Ther. 2013; 21 (4): 720-2). A number of genome editing technologies have emerged in the past decade, including zinc-finger nucleases (ZFNs), transcription activator-like effector nucleases (TALENs), and the RNA-guided CRISPR/Cas nuclease system. The first two technologies use a strategy of tethering endonuclease catalytic domains to DNA binding proteins for inducing targeted DNA double-stranded breaks (DSBs) at specific genomic loci.

CRISPR is an abbreviation of clustered, regularly interspaced, short palindromic repeats (CRISPR), which is part of adaptive immunity in bacteria and archaea. The CRISPR genomic loci encode the Cas9 endonuclease, which forms a targeted RNA-guided endonuclease with specific RNA (sgRNA) complex (Shalem, et al. Science. 2014; 343(6166): 84-7; Chen S, et al. Cell. 2015; 160(6): 1246-60; Mali P, et al. Nat Methods. 2013; 10(10): 957-63; Mali P, et al. Science. 2013; 339(6121): 823-6; O'Connell M R, et al. Nature. 2014; 516(7530): 263-6; Ran F A, et al. Nature. 2015; 520(7546): 186-91; Ran F A, et al. Cell. 2013; 154(6): 1380-9; Sander J D, Joung J K. 2014; 32(4): 347-55; Sternberg S H, et al. Nature. 2014; 507(7490): 62-7; Yin H, et al. Nat Biotechnol. 2014; 32(6): 551-3). Cas9/sgRNA recognizes the protospacer-adjacent motif (PAM) sequence and the complementary 20 nucleotide genomic sequence. Cas9 cuts approximately 3 nucleotides upstream of the PAM in order to induce double-stranded DNA breaks (DSBs), which are repaired by error-prone non-homologous end-joining (NHEJ) or precise homology-directed repair (HOR). Compared to ZFNs and TALENs, the CRISPR/Cas nuclease system is easy to design, highly specific, and well-suited for high throughput and multiplexed gene editing for a variety of cell types and organisms (Kim H, Kim J S. Nat Rev Genet. 2014; 15(5): 321-34; Damian M, Porteus M H. Mol Ther. 2013; 21 (4): 720-2).

Efficient delivery of the components of Cas9/sgRNA can induce gene cutting at the mutated gene site and correct specific gene mutations, achieving a cure of genetic disorders. However, the challenge is formidable and poses important challenges, including efficiency, specificity, and safety. Current repair rate is less than 10% of total cells with mutations reported in the literature. Therefore, improvements in the delivery of the Cas9/sgRNA system are required for potential clinical therapeutic application of genome editing for gene corrections. Delivery of plasmid-encoding Cas9 through hydrodynamic injection and AAV vectors has been demonstrated in the literature and has successfully corrected mutated genes in mouse models (Hsu P D, et al. Nat Biotechnol. 2013; 31 (9): 827-32; Zuris J A, et al. Nat Biotechnol. 2015; 33(1): 73-80). However, potential DNA damage is a significant safety issue if Cas9 is present for an extended period of time. Recently, messenger RNA (mRNA) therapeutics has demonstrated a potential for expressing functional proteins (Tavernier G, et al. J Control Release. 2011; 150(3): 238-47; Pascolo S. et al. Handb Exp Pharmacol. 2008(183): 221-35; Phua K K, et al. J Control Release. 2013; 166(3): 227-33; Mcivor R S. Mol Ther. 2011; 19(5): 622-3; Sahin U, et al. Nat Rev Drug Discov. 2014; 13(10): 759-60; Su X, et al. Mol Pharm. 2011; 8(3): 774-87). Hence, Cas9 protein can be translated through a non-viral delivery of Cas9 mRNA, which would allow for the short-term expression and eventually complete clearance of the nuclease from the body.

In this example, amino ester lipid nanoparticles and AAV vectors are used for the delivery of Cas9/sgRNA system. Lipid nanoparticles deliver mRNA encoding Cas9 and express Cas9 protein. AAV vectors express gRNA and provide repair template DNA. Combination of the two delivery tools as a gene editing system maximizes delivery efficiency and minimizes potential toxicity.

Example 4. Gene Editing Efficiency and Safety Profiles in a Hemophilia B Mouse Model Delivery efficiency of mRNA encoding Cas9 in C57BU6 mice is measured. Briefly, eight-week-old female C57BL/6 mice are classified into four groups: PBS, mRNA alone, lipid alone, and lipid-mRNA groups (5 animals per group). The dose is determined from in vitro potency. After administration, liver Cas9 protein levels at different time points (at 4, 8, 12 and 24 hr) are measured by western blot (Barzel A. et al. Nature, 2015; 517(7534): 360-4). Biodistribution of the top-performing material is also measured. C57BL/6 mice is administered intravenously via tail vein injection for luciferase mRNA expression experiments. The mice are sacrificed at the time point from the above studies; the pancreas, spleen, liver, kidneys, ovaries/uterus, heart, lungs, and thymus as well as a section of the adipose tissue and muscle tissue is then dissected. The tissues is examined with an IVIS imaging system from Caliper.

Figure 10:
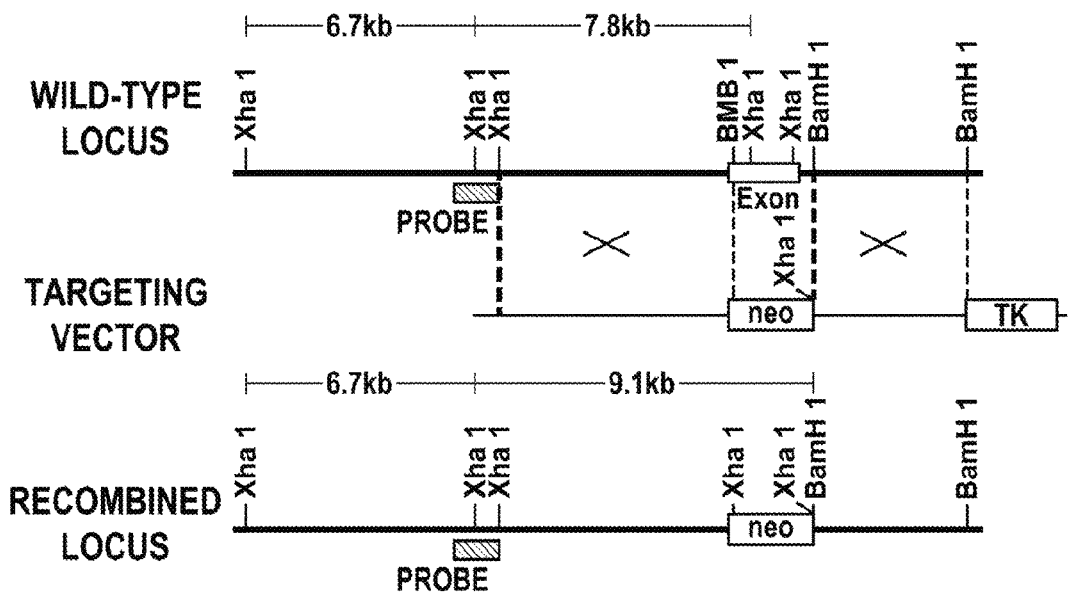
FIG. 10. A schematic illustration of a hemophilia B mouse model. A portion of the mouse factor IX gene showing the last exon, the targeting vector, and the expected recombined locus is depicted. The targeting construct contains a PGK-neo cassette, flanked by DNA fragments upstream and downstream the putative exon 8. The predicted product of successful homologous recombination is shown at the bottom.

A hemophilia B mouse model has been established (FIG. 10; Wang, L. et al. *Proc. Natl. Acad. Sci. U.S.A.* 1997, 94, 11563-11566). AAV vector is constructed using Gibson assembling. AAV9 virus is prepared and purified. In order to determine whether lipid nanoparticles can deliver Cas9 mRNA in HB mice, after tail vein injections of Cas9 mRNA nanoparticles, the expression level of Cas9 protein in total liver lysates is measured by western blot. To measure the half-life of Cas9 mRNA in vivo, total RNA of liver is extracted and measured by qPCR.

CRISPR design and analysis is performed using the website http://crispr.mit.edu developed by Dr. Feng Zhang at MIT. An AAV9 vector has been designed with a U6-sgRNA expression cassette and an HOR template (AAV9-HOR). In order to investigate whether combination of amino ester LLNs and AAV9-HOR is able to induce gene cutting in vivo, these are administered in the hemophilia B mice. These mice possess a PGK-neo cassette at the last exon of FIX (corresponding to human factor IX exon 8), coding for a large portion of the catalytic domain of factor IX. To enable repair of the FIX gene, an AAV vector is designed with a U6-sgRNA expression cassette and an HOR template (AAV9-HOR), which consists of about 1.0 kb homologous sequence to the FIX genomic region on each side of the PGK-neo cassette (FIG. 10).

These are packaged using an AAV9, which has shown the highest efficiency to target the liver compared to other AAV subtypes (Zincarelli C, et al. Mol Ther. 2008; 16(6): 1073-80). 7 days after administration, efficacy is evaluated in HB mice using a number of bioassays including: a tail-bleeding model, whole blood rotation thromboelastometry (ROTEM), activated partial thromboplastin time (aPTT), and platelet-poor plasma (PPP) thrombin generation assays (Barzel A. et al. Nature, 2015; 517(7534): 360-4; Suwanmanee T, et al. Mol Ther. 2014; 22(3): 56774). In order to quantify gene repair rate in vivo, qRT-PCR is performed using primers spanning exons 8 and compare with wild type mice. To further examine genome editing in the liver, deep sequencing of the FIX locus in liver genomic DNA is conducted. The percentage of indels at predicted sgRNA target region in the group treated with amino ester LLNs/AAV9-HDR is also measured.

In addition to efficacy, safety is an important factor for the application of gene corrections in human therapeutics. Cas9/sgRNA may cause indels at off-target genomic sites. In order to investigate potential off-target effects using amino ester LLNs/AAV9-HDR system in vivo, a deep sequencing is conducted at the top five predicted off-target sites. To understand the potential toxicity and immunogenicity of the system, a single-dose and repeat dose tolerability study in mice is performed (Dong Y, et al. PNAS USA, 2014; 111 (11): 3965-60). The clinical signs and body weight in treated groups compared to the control group is measured. Cytokine induction and serum chemistry parameters (alanine transaminase-ALT, aspartate transaminase-AST, and cholesterol) after administration of the materials is also measured (Dahlman J E et al. Nat Nanotechnol. 2014:9(8): 648-55). Lastly, the histology of tissue samples of treated groups in comparison to the control group is analyzed.

Briefly, C57BL/6 mice are administered with the top-performing material via tail vein injection. Blood and tissue samples are collected from the animals. Histopathology on liver, spleen, kidneys, heart, and lungs is processed and evaluated. Immunoassays are used to measure the levels of cytokines in a 96-well plate using Bio-Plex Pro™ assays formatted on magnetic beads. 30 different cytokines are analyzed: IL-1, IL-2, IL-3, IL-4, IL-5, IL-6, IL-9, IL-10, IL-12 (p40), IL-12 (p70), IL-13, IL-17, Exotaxin, G-CSF, GM-CSF, IFN-y, KC, MCP-1, MW-1a, MIP-1b, RANTES, TNG-a, IL-18, FGF-basic, LIF, MCSF, MIG, MIP-2, PDGF-bb and VEGF. Clinical chemistry of ALT, AST, and total bilirubin is measured by ELISA.

A T7E1 assay has been established to analyze the percentage of gene cutting. Cas9 and sgRNAs are transfected in vitro. After genome DNA preparation and PCR reactions, subsequent T7E1 assay is performed to check the cutting of the target gene.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:
1. A compound of Formula I:

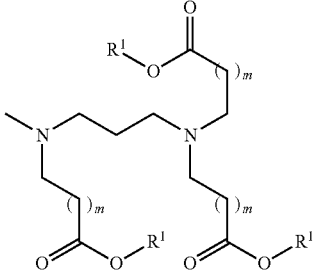

Formula I and salts thereof; wherein
each $R^1$ is independently substituted or unsubstituted alkyl; or substituted or unsubstituted alkenyl;
each m is independently 3, 4, 5, 6, 7, 8, 9, or 10.

2. The compound of claim 1, wherein at least one $R^1$ is unsubstituted alkenyl.

3. The compound of claim 2, wherein at least one $R^1$ is

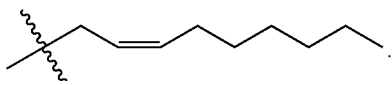 [SMILES: *C/C=C\CCCCCC]

4. The compound of claim 1, wherein at least one $R^1$ is unsubstituted alkyl.

5. The compound of claim 4, wherein at least one $R^1$ is

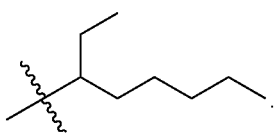

6. The compound of claim 1, wherein at least one m=7.
7. The compound of claim 1, wherein at least one $R^1$ is $C_6$-$C_{10}$ alkenyl.
8. The compound of claim 1, wherein at least one $R^1$ is a branched alkenyl.
9. The compound of claim 1, wherein at least one $R^1$ is $C_6$-$C_{10}$ alkyl.
10. The compound of claim 1, wherein at least one $R^1$ is a branched alkyl.
11. The compound of claim 1, wherein each $R^1$ is unsubstituted alkenyl.
12. The compound of claim 11, wherein each $R^1$ is

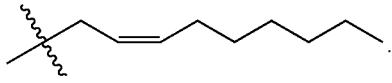 [SMILES: *C/C=C\CCCCCC]

13. The compound of claim 1, wherein each $R^1$ is unsubstituted alkyl.

14. The compound of claim 13, wherein each $R^1$ is

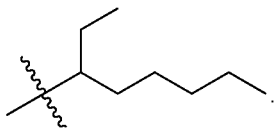

15. The compound of claim 1, wherein each m=7.
16. The compound of claim 1, wherein each $R^1$ is $C_6$-$C_{10}$ alkenyl.
17. The compound of claim 1, wherein each $R^1$ is $C_6$-$C_{10}$ alkyl.
18. The compound of claim 1, wherein each $R^1$ is a branched alkyl.
19. A composition comprising:
a compound of Formula I;

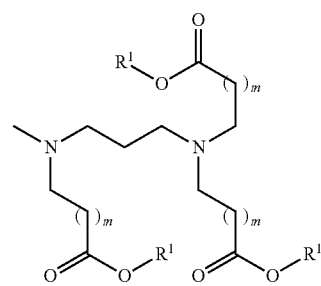

Formula I and salts thereof; wherein
each $R^1$ is independently substituted or unsubstituted alkyl; or substituted or unsubstituted alkenyl;
each m is independently 3, 4, 5, 6, 7, 8, 9, or 10;
and
an agent.

20. A nanoparticle comprising:
a compound of Formula I;

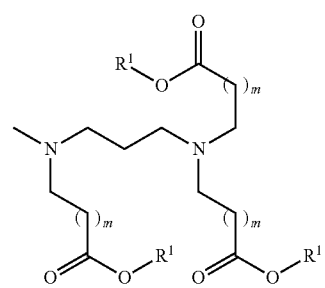

Formula I and salts thereof; wherein
each $R^1$ is independently substituted or unsubstituted alkyl; or substituted or unsubstituted alkenyl;
each m is independently 3, 4, 5, 6, 7, 8, 9, or 10;
a non-cationic lipid;
a polyethylene glycol-lipid; and
a sterol.

* * * * *